US009644242B2

(12) United States Patent
Snoeren et al.

(10) Patent No.: US 9,644,242 B2
(45) Date of Patent: May 9, 2017

(54) RESISTANCE TO ARTHROPOD PEST IN TOMATOES

(71) Applicants: Tjeerd Adrianus Lambertus Snoeren, St Utrecht (NL); Einat Sitbon, Ness Ziona (IL); David Levy, Lapid (IL)

(72) Inventors: Tjeerd Adrianus Lambertus Snoeren, St Utrecht (NL); Einat Sitbon, Ness Ziona (IL); David Levy, Lapid (IL)

(73) Assignee: VILMORIN & CIE, Paris (FR)

( * ) Notice: Subject to any disclaimer, the term of this patent is extended or adjusted under 35 U.S.C. 154(b) by 793 days.

(21) Appl. No.: 13/828,187

(22) Filed: Mar. 14, 2013

(65) Prior Publication Data

US 2014/0283191 A1 Sep. 18, 2014

(51) Int. Cl.

| A01H 5/08 | (2006.01) |
|---|---|
| A01H 1/00 | (2006.01) |
| C12Q 1/68 | (2006.01) |
| A01H 1/04 | (2006.01) |
| C12N 15/00 | (2006.01) |

(52) U.S. Cl.
CPC ............ *C12Q 1/6895* (2013.01); *A01H 1/04* (2013.01); *A01H 5/08* (2013.01); *C12Q 2600/156* (2013.01)

(58) Field of Classification Search
None
See application file for complete search history.

(56) References Cited

U.S. PATENT DOCUMENTS

2009/0241209 A1* 9/2009 Foolad .................... A01H 5/08
800/260

OTHER PUBLICATIONS

Paterson et al., Genetics, 1991, vol. 127, No. 1, pp. 181-198.*
Robert et al., Molecular Breeding, Oct. 2001, vol. 8, No. 3, pp. 217-233.*
Erb W Alan et al: "Resistance of selected interspecific Lycopersicon hybrids to Liriomyza trifolii (Diptera: Agromyzidae)", Journal of Economic Entomology, vol. 86, No. 1, Jan. 1, 1993, pp. 100-109, XP009170727, ISSN: 0022-0493.
Syarifin Firdaus et al: Resistance to Bemisia tabaci in tomato wild relatives, Euphytica, Kluwer Academic Publishers, DO, vol. 187, No. 1, May 18, 2012, pp. 31-45, XP035101709, ISSN: 1573-5060, DOI: 10.1007/S10681-012-0704-2.
Aaron T Simmons et al: "Trichome characteristics of F1 Lycopersicon Esculentum L. Cheesmanii f. Minor and L. Esculentum L. Pennellii hybrids and effects on Myzus persicae", Euphytica, Kluvver Academic Publishers, DO, vol. 144, No. 3, Aug. 1, 2005, pp. 313-320, XP019240963, ISSN: 1573-5060, DOI 10.1007/S10681-005-8002-X.
Villalta I El At: "Comparative QTL analysis of salinity tolerance in terms of fruit yield using two solanum populations of F7 lines",
Theoretical and Applied Genetics; International Journal of Plant Breeding Research, Springer, Berlin, DE, vol. 144, No. 6, Feb. 14, 2007, pp. 1001-1017, XP019510478, ISSN: 1432-2242, DOI: 10.1007/S00122-006-0494-9.
Syarifin Firdaus et al: "Identification and QTL mapping of whitely resistance components in Solarium galapagense" Tag Theoretical and Applied Genetics, vol. 126, No. 6, Jun. 1, 2013, pp. 1487-1507, XP055069088, ISSN: 0040-5752, DOI: 10.1007/S00122-013-2067-Z.
Jul. 12, 2013 European Search Report issued in connection with Europrean Patent Application No. 13305205.0.
de Azevedo et al. (2003). Zingiberene-mediated resistance to the South American tomato pinworm derived from *Lycopersicon hirsutum* var. *hirsutum*. *Euphytica*, 134, 347-351.
Barrett et al. (2005). Haploview: analysis and visualization of LD and haplotype maps. *Bioinformatics*, 21(2), 263-265.
Bombarely et al. (Oct. 8, 2010). The sol genomics network (solgenomics.net): growing tomatoes using Perl. *Nucleic Acids Research*, 39, D1149-D1155.
Broman & Sen (2009). *A guide to QTL Mapping with R/qtl*. New York, NY: Springer.
Ecole et al. (2001). Effect of cropping season and possible compounds involved in the resistance of *Lycopersicon hirsutum* f. *typicum* to *Tuta absoluta* (Meyrick) (Lep., Gelechiidae). *J. Appl. Ent.*, 125, 193-200.
Eigenbrode & Trumble (1993). Resistance to beet armyworm, hemipterans, and *Liriomyza* spp. In *Lycopersicon* Accessions. *J. Amer. Soc. Hort. Sci.*, 118(4), 525-530.
Lewontin (Jan. 10, 1964). The interaction of selection and linkage. I. General considerations; heterotic models. *Genetics*, 49(1), 49-67.
Maluf et al. (1997). 2-Tridecanone-mediated mechanisms of resistance to the South American tomato pinworm *Scrobipalpuloides absoluta* (Meyrick, 1917) (Lepidoptera-Gelechiidae) in *Lycopersicon* spp. *Euphytica*, 93(2), 189-194.
Maluf et al. (2010). Resistance to the South American tomato pinworm *Tuta absoluta* in high acylsugar and/or high zingiberene tomato genotypes. *Euphytica*, 176, 113-123.
Maluf et al. (2010). Broad-spectrum arthropod resistance in hybrids between high- and low-acylsugar tomato lines. *Crop Science*, 50, 439-450.

(Continued)

*Primary Examiner* — Phuong Bui
(74) *Attorney, Agent, or Firm* — John P. White; Cooper & Dunham LLP

(57) ABSTRACT

The present invention is directed to a commercial tomato, namely *S. lycopersicum* plant, which is resistant to an arthropod pest comprising in its genome introgressed sequences from *S. galapagense* conferring resistance to said arthropod pest, wherein the introgressed sequences are chosen from those present in the genome of a plant of the line TUT115 NCIMB accession number 42109. The commercial tomato of the invention is preferably resistant to ToMV (Tomato Mosaic Virus). The introgressed sequences are preferably found at one or more of the 12 loci defined by the following SNP markers: SNP solcap_snp_sl_59890 on chromosome 1, SNP solcap_snp_sl_15339 on chromosome 1, SNP solcap_snp_sl_40154 on chromosome 1, SNP solcap_snp_sl_32320 on chromosome 6, SNP SL10187_425 on chromosome 6, SNP EE_2362 on chromosome 6, SNP EE_2996 on chromosome 6, SNP SL10539_786_LC7260 on chromosome 6, SNP EP_0489_LC7684 on chromosome 9, SNP IL2_5178 on chromosome 9, SNP EE_3482_LC7808 on chromosome 9 and SNP EE_1452 on chromosome 9.

13 Claims, 3 Drawing Sheets

(56) References Cited

OTHER PUBLICATIONS

Momotaz et al. (2010). Identification of quantitative trait loci conferring resistance to *Bemisia tabaci* in an $F_2$ population of *Solanum lycopersicum* x *Solanum habrochaites* Accession LA1777. *J. Amer. Soc. Hort. Sci.*, 135(2), 134-142.

Oliveira et al. (2009). Resistance of 57 greenhouse-grown accessions of *Lycopersicon esculentum* and three cultivars to *Tuta absoluta* (Meyrick) (Lepidoptera: Gelechiidae). *Scientia Horticulturae*, 119, 182-187.

Resende et al. (2002). Inheritance of acylsugar contents in tomatoes derived from an interspecific cross with the wild tomato *Lycopersicon pennellii* and their effect on spider mite repellence. *Genetics and Molecular Research*, 1(2), 106-116.

Resende et al. (2006). Acylsugars in tomato leaflets confer resistance to the South American tomato pinworm, *Tuta absoluta* Meyr. *Sci. Agric. (Piracicaba, Braz.)*, 63(1), 20-25.

Schoonhoven, van Loon, & Dicke (2005). *Insect-Plant Biology* ($2^{nd}$ ed.). New York, NY: Oxford University Press.

Zadoks, Chang, & Konzak (1974). A decimal code for the growth stages of cereals. *Weed Research*, 14(6), 415-421.

Lucatti AF, van Heusden AW, de Vos RC, Visser RG, Vosman B., "Differences in insect resistance between tomato species endemic to the Galapagos Islands." BMC Evol. Biol. Aug. 24, 2013; 13:175.

\* cited by examiner

SEQUENCE LISTING

<160> NUMBER OF SEQ ID NOS: 48

<210> SEQ ID NO 1
<211> LENGTH: 50
<212> TYPE: DNA
<213> ORGANISM: Lycopersicon esculentum

<400> SEQUENCE: 1
caaaatttgg gagagctgaa gcagagtttc ccactcaagg taaatgtata    50

<210> SEQ ID NO 2
<211> LENGTH: 50
<212> TYPE: DNA
<213> ORGANISM: Lycopersicon esculentum

<400> SEQUENCE: 2
agctagtcaa aagtatgcca gttgtgtcct gttgcttgtg tatatagttc    50

<210> SEQ ID NO 3
<211> LENGTH: 50
<212> TYPE: DNA
<213> ORGANISM: Lycopersicon esculentum

<400> SEQUENCE: 3
agtctctaac aatcaagttg gtggggatat aggctcagac attgagctgg    50

<210> SEQ ID NO 4
<211> LENGTH: 50
<212> TYPE: DNA
<213> ORGANISM: Lycopersicon esculentum

<400> SEQUENCE: 4
acattcatct gattccgatc aagaagttga tgattacgat gaccttccac    50

<210> SEQ ID NO 5
<211> LENGTH: 60
<212> TYPE: DNA
<213> ORGANISM: Lycopersicon esculentum

<400> SEQUENCE: 5
gagaaaaaga ccattagaca aagaaaaggt gttttgatag ctacggagaa aaagagaaag    60

<210> SEQ ID NO 6
<211> LENGTH: 60
<212> TYPE: DNA
<213> ORGANISM: Lycopersicon esculentum

<400> SEQUENCE: 6
atagagaaaa aaagcaaaac agggagatga aagggtctc taatgggaga tccattccct    60

<210> SEQ ID NO 7
<211> LENGTH: 60
<212> TYPE: DNA
<213> ORGANISM: Lycopersicon esculentum

<400> SEQUENCE: 7
taaactaaag tctccttta tttttcatca ataaccttat aactaactta actaaaaaca    60

<210> SEQ ID NO 8
<211> LENGTH: 60
<212> TYPE: DNA
<213> ORGANISM: Lycopersicon esculentum

<400> SEQUENCE: 8 aggcaattt tatccacacc aaatataaaa ctaaacttaa atccccattt tccaagacat    60

<210> SEQ ID NO 9
<211> LENGTH: 60
<212> TYPE: DNA
<213> ORGANISM: Lycopersicon esculentum

<400> SEQUENCE: 9
ctgaaggtcc agaccacctg tactgcccct ctccacacct atgtccagca taaggacact    60

<210> SEQ ID NO 10
<211> LENGTH: 60
<212> TYPE: DNA
<213> ORGANISM: Lycopersicon esculentum

<400> SEQUENCE: 10

```
ctaaagctga gtctttgatg gaaaaaatgt ctgaatgcgg ggttctgaag taccctcttc    60
```

<210> SEQ ID NO 11
<211> LENGTH: 100
<212> TYPE: DNA
<213> ORGANISM: Lycopersicon esculentum

<400> SEQUENCE: 11

```
aataatctcc cctcctttaa acttggagta tttgaatatc actgtttccg atccacacaa    60
ggaaatacaa gcatccccct caattgttcc tggcactaat                         100
```

<210> SEQ ID NO 12
<211> LENGTH: 100
<212> TYPE: DNA
<213> ORGANISM: Lycopersicon esculentum
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t

<400> SEQUENCE: 12

```
cttatgtnac ctatttaatt accacacaaa ccaatttacc tgattatgga ggaaccgatt    60
tcantgttcg tagacgcttt aaagacattg ttactttatc                         100
```

<210> SEQ ID NO 13
<211> LENGTH: 60
<212> TYPE: DNA
<213> ORGANISM: Lycopersicon esculentum

<400> SEQUENCE: 13

```
gatgatgaaa aggtggatta ttcacaagta ctttctgcat tgcttccttt tgttgtggcc    60
```

<210> SEQ ID NO 14
<211> LENGTH: 60
<212> TYPE: DNA
<213> ORGANISM: Lycopersicon esculentum

<400> SEQUENCE: 14

```
tcactgctgt tgctgctctt tctcacccct caactttcac atgggtttct aaagatttgt    60
```

<210> SEQ ID NO 15
<211> LENGTH: 56
<212> TYPE: DNA
<213> ORGANISM: Lycopersicon esculentum

<400> SEQUENCE: 15

```
gccggggata gctaacacac caatattatt aatttagaga atcaattatg gagatc        56
```

<210> SEQ ID NO 16
<211> LENGTH: 60
<212> TYPE: DNA
<213> ORGANISM: Lycopersicon esculentum

<400> SEQUENCE: 16

```
atgggaactc aaatgatgtt cttcacatag ttttgttccc ttttttttcgc atttggtcat   60
```

<210> SEQ ID NO 17
<211> LENGTH: 60
<212> TYPE: DNA

<210> SEQ ID NO 17
<211> LENGTH: 60
<212> TYPE: DNA
<213> ORGANISM: Lycopersicon esculentum

<400> SEQUENCE: 17
aagttgcaag agttgctttt gcctcgcttc tcttgttgat gctgatgcta tagtaacttc    60

<210> SEQ ID NO 18
<211> LENGTH: 60
<212> TYPE: DNA
<213> ORGANISM: Lycopersicon esculentum

<400> SEQUENCE: 18
gaatgggttc ctaccattga ccaaatgctt ctcatgacca gcatagtcct tacatatata    60

<210> SEQ ID NO 19
<211> LENGTH: 60
<212> TYPE: DNA
<213> ORGANISM: Lycopersicon esculentum

<400> SEQUENCE: 19
gtctagtatt gttgtaagaa tgctggaaga ggcatttgtg attataaaag aaacttggca    60

<210> SEQ ID NO 20
<211> LENGTH: 60
<212> TYPE: DNA
<213> ORGANISM: Lycopersicon esculentum

<400> SEQUENCE: 20
gatataggtt ataacacagc ataaatctat atctaattca cttgaacatt acacaagaag    60

<210> SEQ ID NO 21
<211> LENGTH: 50
<212> TYPE: DNA
<213> ORGANISM: Lycopersicon esculentum

<400> SEQUENCE: 21
ggcttcaata ttgactgtaa tgaaggagat ttctgataca ttgtacccaa    50

<210> SEQ ID NO 22
<211> LENGTH: 50
<212> TYPE: DNA
<213> ORGANISM: Lycopersicon esculentum

<400> SEQUENCE: 22
gcctgtcgtg atttttaatc ctaaatgggg ttttgatgaa gagagtagtt    50

<210> SEQ ID NO 23
<211> LENGTH: 60
<212> TYPE: DNA
<213> ORGANISM: Lycopersicon esculentum

<400> SEQUENCE: 23
tattacggaa tctactgtaa cgttatcaga agctctgtct gaacttccag gtgaaaggac    60

<210> SEQ ID NO 24
<211> LENGTH: 60
<212> TYPE: DNA
<213> ORGANISM: Lycopersicon esculentum

<400> SEQUENCE: 24
gaaggtggtt ctatatccct agatgccttg tcttgcgaga accatgaaat aaagaagatg    60

<210> SEQ ID NO 25
<211> LENGTH: 60

<212> TYPE: DNA
<213> ORGANISM: Lycopersicon esculentum

<400> SEQUENCE: 25
gtcgcaagat gcgtgagatc atggttaacc aggcacaatc gtgtgatttg aaagacttgg    60

<210> SEQ ID NO 26
<211> LENGTH: 60
<212> TYPE: DNA
<213> ORGANISM: Lycopersicon esculentum

<400> SEQUENCE: 26
cctgaagttc attcctgaat caatcggtag agagattgag aaggcaactt caagcatcta    60

<210> SEQ ID NO 27
<211> LENGTH: 60
<212> TYPE: DNA
<213> ORGANISM: Lycopersicon esculentum

<400> SEQUENCE: 27
atgggttggt tttggagaac atatcgtatg ggcagcttca ggcgctttca gctgtgcctg    60

<210> SEQ ID NO 28
<211> LENGTH: 60
<212> TYPE: DNA
<213> ORGANISM: Lycopersicon esculentum

<400> SEQUENCE: 28
agatagtcac tctttgttga ctgaggaaag aggcggggaa ggtagtggga gtggttcata    60

<210> SEQ ID NO 29
<211> LENGTH: 60
<212> TYPE: DNA
<213> ORGANISM: Lycopersicon esculentum

<400> SEQUENCE: 29
ttactcttcg gtgtttgagg atcttgttgc agagggtttt ttgagcccaa attcaaaaac    60

<210> SEQ ID NO 30
<211> LENGTH: 60
<212> TYPE: DNA
<213> ORGANISM: Lycopersicon esculentum

<400> SEQUENCE: 30
ctttgcgttg aaacaccgat gggttctgat gttttgcgt tgagggaaat tggggtagcc    60

<210> SEQ ID NO 31
<211> LENGTH: 60
<212> TYPE: DNA
<213> ORGANISM: Lycopersicon esculentum

<400> SEQUENCE: 31
agttccaatt cacgaaatcg aagccttcca actctcatcc acgcttggtg attgcaaagg    60

<210> SEQ ID NO 32
<211> LENGTH: 60
<212> TYPE: DNA
<213> ORGANISM: Lycopersicon esculentum

<400> SEQUENCE: 32
cttggggacc ggcgataatg gtgactttga acattttaca gctacaccta acaagatttt    60

<210> SEQ ID NO 33

```
<211> LENGTH: 50
<212> TYPE: DNA
<213> ORGANISM: Lycopersicon esculentum

<400> SEQUENCE: 33
tttttacttt taaattttgc tgtttgtgaa gtagggatat gaataaaatt          50

<210> SEQ ID NO 34
<211> LENGTH: 50
<212> TYPE: DNA
<213> ORGANISM: Lycopersicon esculentum

<400> SEQUENCE: 34 ttggtcccett cttgtacaat aggaatgtaa gaactagcat atgagggatc          50

<210> SEQ ID NO 35
<211> LENGTH: 50
<212> TYPE: DNA
<213> ORGANISM: Lycopersicon esculentum

<400> SEQUENCE: 35
aagagggcaa aaaatggctg tagcactctt ggggagtatt tccttttcct          50

<210> SEQ ID NO 36
<211> LENGTH: 50
<212> TYPE: DNA
<213> ORGANISM: Lycopersicon esculentum

<400> SEQUENCE: 36
ctccatgcct tctatatctt ccccttctct ccaacaccct ttcaacttca          50

<210> SEQ ID NO 37
<211> LENGTH: 50
<212> TYPE: DNA
<213> ORGANISM: Lycopersicon esculentum

<400> SEQUENCE: 37
aacgccagca atggaaaagc aacttgagat cgcgtccaca gttggtgcat          50

<210> SEQ ID NO 38
<211> LENGTH: 50
<212> TYPE: DNA
<213> ORGANISM: Lycopersicon esculentum

<400> SEQUENCE: 38
ggttgctaaa tccaaccagc ccaatgaagt aggtgatttt ggtggtagtt          50

<210> SEQ ID NO 39
<211> LENGTH: 50
<212> TYPE: DNA
<213> ORGANISM: Lycopersicon esculentum

<400> SEQUENCE: 39
ggcgcctaga actgcttctt cttttcttgt gacgcgaact tctgtctctt          50

<210> SEQ ID NO 40
<211> LENGTH: 50
<212> TYPE: DNA
<213> ORGANISM: Lycopersicon esculentum

<400> SEQUENCE: 40
tctcatccaa ccactcactg ctggaatctg tattacgatc ttccttgcta          50
```

```
<210> SEQ ID NO 41
<211> LENGTH: 50
<212> TYPE: DNA
<213> ORGANISM: Lycopersicon esculentum

<400> SEQUENCE: 41
atgttaactg aaattgcata catccacgtt aacaggaaaa catcgtagtc           50

<210> SEQ ID NO 42
<211> LENGTH: 50
<212> TYPE: DNA
<213> ORGANISM: Lycopersicon esculentum

<400> SEQUENCE: 42
cttctagcaa gaactttta ccctgtaatt tgaaatccaa caaacccaga            50

<210> SEQ ID NO 43
<211> LENGTH: 60
<212> TYPE: DNA
<213> ORGANISM: Lycopersicon esculentum

<400> SEQUENCE: 43 aaacccaat ttctccggcc gatcagttct cctctttgtt gatctcattt ttcgattctc   60

<210> SEQ ID NO 44
<211> LENGTH: 60
<212> TYPE: DNA
<213> ORGANISM: Lycopersicon esculentum

<400> SEQUENCE: 44
gatcacttta cagatccgat ttcgagtcac ttccgaatcg gatccgggtc agatggcggc   60

<210> SEQ ID NO 45
<211> LENGTH: 60
<212> TYPE: DNA
<213> ORGANISM: Lycopersicon esculentum

<400> SEQUENCE: 45
ctagacagta gtgaccaaac tcttggtgtt ccgcgtaagt tttagagtat aataaaccca   60

<210> SEQ ID NO 46
<211> LENGTH: 60
<212> TYPE: DNA
<213> ORGANISM: Lycopersicon esculentum

<400> SEQUENCE: 46
aggactcgaa aaacattagc tcagatgatg atgaccttgt gtaaattttc gtattggtat   60

<210> SEQ ID NO 47
<211> LENGTH: 60
<212> TYPE: DNA
<213> ORGANISM: Lycopersicon esculentum

<400> SEQUENCE: 47
ctctagccca tcctttatac acagaagggc gcagccacat cgggagttcc tggacgaaca   60

<210> SEQ ID NO 48
<211> LENGTH: 60
<212> TYPE: DNA
<213> ORGANISM: Lycopersicon esculentum

<400> SEQUENCE: 48
agcatggagt caagttttg ctgaatcttc tgttatttaa aattgataga gacttaccac    60
```

RESISTANCE TO ARTHROPOD PEST IN TOMATOES

This application incorporates-by-reference nucleotide and/or amino acid sequences which are present in the file named "130314_0857_85043_Sequence_Listing_GC.txt," which is 7.89 kilobytes in size, and which was created Mar. 13, 2013 in the IBM-PC machine format, having an operating system compatibility with MS-Windows, which is contained in the text file filed Mar. 14, 2013 as part of this application.

The present invention relates to tolerance or resistance in plants of *Solanum lycopersicum*, also known as *Lycopersicum esculentum*, to arthropod pests, especially to the South American tomato pinworm, *Tuta absoluta*. According to the invention, the resistance or tolerance is provided by DNA sequences, introgressed from *S. galapagense* at corresponding specific loci in the genome of a *S. lycopersicum* plant. The introgressed sequences can be present homozygously or heterozygously in the genome of the *S. lycopersicum* plant, and they confer tolerance or resistance to said pests.

BACKGROUND OF THE INVENTION

The South American tomato pinworm, *T. absoluta* (Lepidoptera—Gelechiidae also known as *Scrobipalpula absoluta, Scrobipalpuloides absoluta, Gnorimoschema absoluta*, and *Phthorimaea absoluta*) is one of the most severe pests for solanaceous plants, especially tomatoes. According to Maluf et al. (Euphytica, 2010, 176:113-123), *T. absoluta* is an insect of neotropical distribution considered as a major tomato pest in several Latin American countries, including Argentina, Chile, Peru, Bolivia, Ecuador, Colombia, Venezuela, Uruguay and Brazil. It was reported for the first time in Europe in 2006, in the Spanish province of Castellon, and has since been reported in other parts of Spain (Valencia, Ibiza, Almeria, Murcia and Catalunya) and of the Mediterranean basin, including tomato-producing areas of Morocco and Algeria, and more recently in Israel, Turkey, Syria, Germany, Hungary, Lithuania and Serbia.

*T. absoluta* attacks the plants in all of their developmental stages, damaging the leaf mesophyll, stems, stem apexes, flowers and fruits. According to Maluf et al., oviposition of *T. absoluta* is predominantly on leaflets (on both abaxial and adaxial surfaces) of the upper third of the plant, but can also occur in stems and flowers. Larvae feed predominantly on leaf parenchyma tissue, on tender portions of the stems (especially axillary buds), and in both developing and mature fruit. Leaf mining can evolve until all the parenchyma tissue of the leaves is consumed and only leaf veins and insect frass are left. Severe pinworm attack can cause yield losses of up to 100%.

*T. absoluta* is thus considered as a limiting factor for tomato production in several Latin American countries, wherein it accounts for about 70% of the losses and it becomes an increasing concern in Europe.

Control of this pest currently requires heavy application of insecticides. However, the increase of resistance of this pinworm to insecticides is reported. Moreover, blanket spraying of insecticides is harmful to both man and the environment.

Therefore, enhanced resistance of commercial tomato against the pinworm by introducing antixenosis and/or antibiosis resistance traits, or enhanced tolerance, is increasingly appreciated by commercial growers. So far such resistance or tolerance in a commercial tomato has not been reported against the pinworm.

In this context, varietal resistance to *T. absoluta* in tomatoes may be an important component of pest management programs. Resistance to *T. absoluta* has been found in several wild tomato accessions, inter alia in *S. pennellii* (corresponding to *L. pennellii*) LA716, *S. peruvianum* NAV29 and NAV 115, *S. habrochaites* (also named *L. hirsutum*) var. *glabratum* PI 134418 and PI 134417, *S. habrochaites* (also named *L. hirsutum*) var. *hirsutum* PI 127826, and *L. hirsutum* f. *typicum* LA1777 (Ecole, 2001). Resistance in these species is thought to be largely mediated by allelochemicals with pest-deterrent activities, such as methyl-ketones in PI 134417 (Maluf et al. 1997), sesquiterpenes (zingiberene) in PI127826 (Azevedo et al. 2003), and acylsugars (acylglucoses, acylfructoses) in LA 716 (Resende et al. 2006; Maluf et al. 2010).

These accessions were used extensively to develop commercial lines of *S. lycopersicum* with good levels of pest-resistance, especially resistance to *T. absoluta*. Maluf et al. (2010a and 2010b) report three proprietary precommercial breeding lines with high leaf acylsugars contents, presenting resistance to the South American tomato pinworm *T. absoluta*. The lines are however not commercial *S. lycopersicum*. Moreover, the resistance level of these lines and hybrid combinations made with them is far less than the resistant parent. No commercial hybrid varieties have apparently been obtained up to now from these 3 lines.

A few QTL analyses carried out in the progeny of some interspecific crosses between resistant wild tomato accessions and *S. lycopersicum* are also reported in the literature (Momotaz et al., 2010). They mainly emphasized the complexity of the resistance traits.

Therefore, in spite of intensive work in this respect and the importance of tomato production in the world, currently no tomato cultivars resistant to pinworm have been obtained though introgression of the trait from a wild tomato accession.

The difficulties encountered by breeders trying to develop commercial varieties from the wild tomato accessions have been so far explained by complex resistance traits, undesirable linkages, or both, and they have hampered efforts to incorporate the pinworm resistance to *L. esculentum* breeding lines and cultivars (see Eigenbrode et al., 1993).

In order to circumvent these difficulties, some authors have proposed as an alternative to use genetic resources of cultivated *S. lycopersicum* maintained in the germplasm banks. It was indeed hypothesized that the absence of known cultivated tomato variety resistant to *T. absoluta* could be associated with reduced genetic variability introduced during tomato domestication, leading to the loss of genes that control the production of allelochemicals involved in plant defenses. Recovery of this lost genetic variability was thus expected to improve plant resistance to pests and diseases (Oliveira et al., 2009). From this study, only two out of 57 accessions appear to present an allegedly promising resistance. The transfer of resistance factors from these accessions to commercial tomato has however not been carried out and no resistant commercial cultivar obtained to date.

There is thus an important need in the art to identify a reliable source of resistance or tolerance, which could be used to obtain resistant or tolerant commercial plants, and a need for improved commercial *S. lycopersicum* plants that are resistant to *T. absoluta* infestation.

The present invention provides commercial *S. lycopersicum* plants that display important tolerance or resistance to *T. absoluta* infestation, as well as methods that produce or identify *S. lycopersicum* plants or populations (germplasm) that display resistance to *T. absoluta* infestation. The present invention also discloses molecular genetic markers, especially SNPs, linked to the resistance loci.

DETAILED DESCRIPTION OF THE INVENTION

The present inventors have identified a wild tomato accession in S. galapagense (also known as L. cheesmanii) which displays an important tolerance or resistance to T. absoluta infestation and they have been able to introgress into S. lycopersicum background the S. galapagense sequences conferring this resistance and/or tolerance, thus obtaining commercial tomatoes resistant and/or tolerant to arthropod pests, especially to T. absoluta. In this process, the present inventors have identified a source of T. absoluta resistance which has never been tested before, namely in a S. galapagense accession. Moreover, in the transfer of the resistance sequences, the inventors have made the main selection steps on the basis of T. absoluta resistance and they have determined the best parameter to be followed for this selection.

It is indeed to be noted that, in the prior art, a direct selection for pest resistance has generally not been carried out in programs for introgression of arthropod resistance into tomato cultivars, due to difficulties in maintaining the uniform infestations necessary to select for resistance and because direct selection for pest resistance is usually an expensive and slow process. Therefore, the prior art is replete with indirect selection techniques, based generally on correlated traits with high heritability to speed up introgression, especially presence of given allelochemicals or type of trichomes.

However, during the selection process of lines and hybrids on the basis of high allelochemical content only, other resistance-related traits that are present in the wild accessions are probably lost and thus not recovered in the selected lines and hybrids. The introgression programs disclosed in the prior art have thus failed to provide a high level of resistance in a commercial tomato line or variety.

By selection directly at the level of pest resistance, the present inventors have been able to introgress the main S. galapagense sequences responsible for resistance, and not only a subset conferring only insufficient resistance. This direct selection has been made possible thanks to the identification of the best parameters to be followed during selection of resistant plants. In this respect, it is noted that the prior art discloses numerous different parameters, such as arthropod eggs and offspring counts, number of large mines per leaf, number of small mines per leaf, percentage of leaves mined, overall plant damage, leaflet lesion type, percent of attacked leaflets, overall leaf damage, and insect survival. Without prior identification of the most powerful parameter, direct selection was not feasible since the nature of the resistance is not entirely clear, likely combining non-preference, antibiosis, antixenosis and tolerance.

The inventors have indeed detected variance in between lines in terms of number of leaflets per total marked leaf fed on (PLA) and the total amount of plant tissue fed on (OPD). This observation could have been caused by differences in amount of eggs the plant was exposed to or the quality of the leaf tissue fed on. The amount of eggs has been ruled out by the inventors, since egg counts per marked leaves indicated no differences between lines. Thus the only causal factor for the non-preference is the quality of the leaf tissue that influences negatively the feeding behavior of the pest, and especially the South American tomato pinworm.

On the basis of the PLA rating, the plants according to the invention thus present an improved tolerance or resistance to arthropod pests by comparison to any commercial S. lycopersicum plant, all the commercial tomatoes before the present invention being indeed susceptible to arthropod pests, especially to T. absolute.

According to a first aspect, the present invention is thus directed to a S. lycopersicum plant, which is tolerant or resistant to an arthropod pest, comprising in its genome introgressed sequences or intervals from S. galapagense conferring resistance to said arthropod pest.

The term "Resistance" is as defined by the ISF (International Seed Federation) Vegetable and Ornamental Crops Section for describing the reaction of plants to pests or pathogens, and abiotic stresses for the Vegetable Seed Industry.

Specifically, by resistance, it is meant the ability of a plant variety to restrict the growth and development of a specified pest or pathogen and/or the damage they cause when compared to susceptible plant varieties under similar environmental conditions and pest or pathogen pressure. Resistant varieties may exhibit some disease symptoms or damage under heavy pest or pathogen pressure.

Insect-resistance refers to insect-plant interactions that comprise insect-responses and plant characteristics,
- Non-preference: refers to insect responses subject to plant characteristics that lead away from the use of a particular plant for oviposition, for food or for shelter, or for combinations of the three.
- Antixenosis: refers to plant characteristics evoking a negative response or a total avoidance by insects.
- Antibiosis: refers to plant characteristics that adversely affect the physiology of a herbivore insect species. Those plant properties denote reduced fecundity, decreased size, reduced longevity and increased mortality of the pest insect species (Schoonhoven et al. 1998).

By tolerance is meant the ability of a plant variety to endure biotic and abiotic stress without serious consequences for growth, appearance and yield.

Susceptibility: The inability of a plant variety to restrict the growth and development of a specified pest or pathogen. Plants from for example the lines Rehovot-13 (LYCO2), Komeett, Plaisance or F1 Daniela (HA144) are susceptible S. lycopersicum plants. A plant according to the invention has thus at least improved resistance or tolerance with respect to these plants, and more generally with respect to any commercial variety of tomato.

By introgression, it is meant the infiltration of the genes or of genomic sequences of one species into the gene pool of another one from an initial interspecific hybrid between these species. Regarding the introgressed sequences or intervals from S. galapagense conferring the tolerance or resistance in S. lycopersicum, they are chosen from those present in the genome of a plant of the tomato seed TUT115. A sample of this tomato seed has been deposited by Hazera Genetics Ltd, Berurim, M. P. Shikmim 79837, Israel, pursuant to, and in satisfaction of, the requirements of the Budapest Treaty on the International Recognition of the Deposit of Microorganisms for the Purposes of Patent Procedure (the "Budapest treaty") with the National Collection of Industrial, Food and Marine Bacteria (NCIMB), (NCIMB Ltd, Ferguson Building, Craibstone Estate, Bucksburn, Aberdeen AB21 9YA, United Kingdom), on 11 Feb. 2013, under accession number NCIMB42109.

A deposit of this tomato seed is maintained by Hazera Genetics Ltd, Berurim, M. P. Shikmim 79837, Israel.

The deposited seeds and plants thereof have been obtained from an initial interspecific cross between a plant of *S. galapagense* GALA1, i.e. the introgression partner displaying the phenotype of interest, and a plant of the line *S. lycopersicum* LYCO1, the recurrent susceptible parent. The deposited seeds thus represent a reservoir of introgressed sequences from *S. galapagense* in the *S. lycopersicum* genome. The introgressed sequences conferring resistance and/or tolerance to pest arthropods according to the invention are chosen from this reservoir.

Preferably, a *S. lycopersicum* plant according to the invention is a commercial plant or line. Such a commercial plant or line preferably also exhibits resistance to ToMV (tomato mosaic virus), for example due to the presence of a Tm-2 (allele Tm-2 or Tm-$2^2$ (also known as Tm-$2^a$)) or Tm-1 resistance gene, which also confers resistance to TMV (Tobacco Mosaic Virus). A plant according to this aspect of the invention preferably has also the following additional features: nematode resistance trait (Mi-1 or Mi-j).

Moreover, the commercial plant of the invention gives rise to fruits in suitable conditions, which are at least 10 grams at maturity, preferably at least 25 g at full maturity and or even more preferred at least 50 g at full maturity.

With regard to the desired phenotype, i.e. tolerance or resistance to arthropod pest, of a plant according to the invention, such a phenotype is conferred by introgressed sequences or intervals from *S. galapagense*, chosen from the introgressed sequences found in the genome of the deposited plants TUT115. Said introgressed sequences or intervals may form part of larger introgression fragments from *S. galapagense* into the genome of a *S. lycopersicum* plant of the invention.

Introgression fragments or introgressed intervals from *S. galapagense* comprising sequences conferring resistance or tolerance to said pest can be found preferably on chromosomes 1, 5, 6, 9 and 12 of a *S. lycopersicum* plant of the invention.

According to a first embodiment of the invention, said introgression fragments and thus said introgressed sequences conferring resistance and/or tolerance to arthropod pests are to be found at one or more of the following loci:
 a) Locus encompassing SNP solcap_snp_sl_18619 on chromosome 1,
 b) Locus encompassing SNP solcap_snp_sl_12348 on chromosome 1,
 c) Locus encompassing SNP EP_1592_LC7762 on chromosome 1,
 d) Locus encompassing SNP EE_0301 on chromosome 5,
 e) Locus encompassing SNP EE_4363_LC7656 on chromosome 6,
 f) Locus encompassing SNP CL016475-0340 on chromosome 9,
 g) Locus encompassing SNP EP_0502 on chromosome 9,
 h) Locus encompassing SNP EE_4969_LC7529 on chromosome 9,
 i) Locus encompassing SNP EE_2332 on chromosome 9,
 j) Locus encompassing SNP SL10204_1269 on chromosome 12,
 k) Locus encompassing SNP SGN-U573565_snp665 on chromosome 12 and
 l) Locus encompassing SNP EE_0924 on chromosome 12.

The 12 SNPs mentioned above are referred to in the following as the 12 SNPs of the invention. Their location in the tomato genome sequence build SL2.40 is indicated in table 7, and their flanking sequences are illustrated in table 10.

On the basis of the tomato genome version SL2.40, said introgressed sequences are to be found at one or more of the following 12 loci:
 a) Locus encompassing position 68 232 900 on chromosome 1,
 b) Locus encompassing position 72 528 600 on chromosome 1,
 c) Locus encompassing position 83 766 400 on chromosome 1,
 d) Locus encompassing position 3 636 270 on chromosome 5,
 e) Locus encompassing position 166 755 on chromosome 6,
 f) Locus encompassing position 22 094 800 on chromosome 9,
 g) Locus encompassing position 41 847 000 on chromosome 9,
 h) Locus encompassing position 49 173 600 on chromosome 9,
 i) Locus encompassing position 54 692 600 on chromosome 9,
 j) Locus encompassing position 124 598 on chromosome 12,
 k) Locus encompassing position 155 493 on chromosome 12 and
 l) Locus encompassing position 1 166 000 on chromosome 12.

By "introgressed sequences or intervals from *S. galapagense* at a given locus" or "introgressed sequences or intervals from *S. galapagense* present/found at a given locus", it is to be understood that the genomic interval found at this given locus has the same sequence as the genomic interval found in *S. galapagense* donor, the introgression partner, at the same locus; thus at least the allele of the SNP is the allele found in the genome of *S. galapagense* donor, and that the 5' flanking region, or the 3' flanking region, or both, are identical to *S. galapagense* sequences in this region. Therefore, the SNP may form part of the 3' border or 5' border of the introgressed interval, or may be within the introgressed interval conferring the desired phenotype.

Said introgressed sequences or intervals are preferably at least 5 kilobases long, and preferably at least 8, 10 or 15 kb long.

Preferably, the introgressed sequences or intervals from *S. galapagense* are not too long in order to avoid introgression of non-commercial features associated with the *S. galapagense* genotype. It is thus preferred according to the invention that the introgressed sequences mentioned above are less than 25 cM each in length, preferably less than 10 cM and most preferably less than 5 cM in order to avoid or limit linkage drag.

According to a preferred embodiment, said introgressed sequences are minimized to contain as few as possible sequences unrelated to the desired phenotype.

More generally, insofar as resistance or tolerance to arthropod pest can be seen as a quantitative phenotype, the specific chromosomal intervals (or QTL for quantitative trait loci) that correlate with the desired phenotype can be mapped by the 12 SNPs recited above.

The introgressed sequences at the 12 loci mentioned above thus constitute Quantitative Trait Loci (QTL) underlying the desired trait.

Regarding the introgressed sequences or intervals from *S. galapagense* conferring the tolerance or resistance, they are chosen from those present in the genome of a plant corresponding to the deposited material TUT115 (NCIMB 42109) at the corresponding loci. Plants corresponding to the deposited material indeed have introgressed sequences from the *S. galapagense* donor GALA1 at said 12 loci.

A plant according to this embodiment thus encompasses in its genome introgressed sequences from *S. galapagense* at one locus or more of the 12 loci recited above; such a plant thus presents the allele specific of the donor *S. galapagense* for at least one of the 12 SNPs recited above. A plant of the invention has thus at least one of the following alleles: allele G of SNP solcap_snp_sl_18619 on chromosome 1, allele C of SNP solcap_snp_sl_12348 on chromosome 1; allele C of SNP EP_1592_LC7762 on chromosome 1, allele T of SNP EE_0301 on chromosome 5, allele G of SNP EE_4363_LC7656 on chromosome 6, allele A of SNP CL016475-0340 on chromosome 9; allele C of SNP EP_0502 on chromosome 9, allele A of SNP EE_4969_LC7529 on chromosome 9, allele T of SNP EE_2332 on chromosome 9, allele C of SNP SL10204_1269 on chromosome 12, allele A of SNP SGN-U573565_snp665 on chromosome 12 and allele T of SNP EE_0924 on chromosome 12.

According to a second embodiment of the invention, said introgression fragments and thus said introgressed sequences conferring resistance and/or tolerance to arthropod pests are alternatively to be found at one or more of the following loci:
a') Locus encompassing SNP solcap_snp_sl_59890 on chromosome 1,
b') Locus encompassing SNP solcap_snp_sl_15339 on chromosome 1,
c') Locus encompassing SNP solcap_snp_sl_40154 on chromosome 1,
d') Locus encompassing SNP solcap_snp_sl_32320 on chromosome 6,
e') Locus encompassing SNP SL10187_425 on chromosome 6,
f') Locus encompassing SNP EE_2362 on chromosome 6,
g') Locus encompassing SNP EE_2996 on chromosome 6,
h') Locus encompassing SNP SL10539_786_LC7260 on chromosome 6,
i') Locus encompassing SNP EP_0489_LC7684 on chromosome 9,
j') Locus encompassing SNP IL2_5178 on chromosome 9,
k') Locus encompassing SNP EE_3482_LC7808 on chromosome 9, and
l') Locus encompassing SNP EE_1452 on chromosome 9.

These 12 SNPs will be referred to in the following as the 12 alternative SNPs of the invention. Their location in the tomato genome sequence build SL2.40 is indicated in table 7, and their flanking sequences are illustrated in table 10.

On the basis of the tomato genome version SL2.40, said introgressed sequences are to be found at one or more of the following 12 loci:
a') Locus encompassing position 4 597 950 on chromosome 1,
b') Locus encompassing position 77 112 400 on chromosome 1,
c') Locus encompassing position 83 517 400 on chromosome 1,
d') Locus encompassing position 5 388 530 on chromosome 6,
e') Locus encompassing position 12 751 900 on chromosome 6,
f') Locus encompassing position 29 418 200 on chromosome 6,
g') Locus encompassing position 34 459 100 on chromosome 6,
h') Locus encompassing position 35 194 800 on chromosome 6,
i') Locus encompassing position 3 897 960 on chromosome 9,
j') Locus encompassing position 7 854 930 on chromosome 9,
k') Locus encompassing position 63 350 800 on chromosome 9, and
l') Locus encompassing position 63 642 500 on chromosome 9.

More generally, insofar as resistance or tolerance to arthropod pest can be seen as a quantitative phenotype, the specific chromosomal intervals (or QTL) that correlate with the desired phenotype can be mapped by the 12 alternative SNPs recited above.

The introgressed sequences at the 12 alternative loci mentioned above thus constitute Quantitative Trait Loci (QTL) underlying the desired trait.

Regarding the introgressed sequences or intervals from *S. galapagense* conferring the tolerance or resistance, they are chosen from those present in the genome of a plant corresponding to the deposited material TUT115, NCIMB accession number 42109.

The preferred minimal length of the introgressed sequences, as well as the preferred maximal length of such sequences, are as defined in the preceding section with respect to the first embodiment of the invention, in connection with the 12 loci of the invention.

A plant according to this embodiment thus encompasses in its genome introgressed sequences from *S. galapagense* at one locus or more of the 12 alternative loci recited above; such a plant thus exhibits the allele specific of the donor *S. galapagense* for at least one of the 12 alternative SNPs. A plant of the invention according to this embodiment has thus at least one of the following alleles: allele A of SNP solcap_snp_sl_59890 on chromosome 1, allele C of SNP solcap_snp_sl_15339 on chromosome 1; not allele T or G of SNP solcap_snp_sl_40154 on chromosome 1, allele C of SNP solcap_snp_sl_32320 on chromosome 6, allele A of SNP SL10187_425 on chromosome 6, allele C of SNP EE_2362 on chromosome 6; allele C of SNP EE_2996 on chromosome 6, allele T of SNP SL10539_786_LC7260 on chromosome 6, allele C of SNP EP_0489_LC7684 on chromosome 9, not allele T or C of SNP IL2_5178 on chromosome 9, allele C of SNP EE_3482_LC7808 on chromosome 9 and allele T of SNP EE_1452 on chromosome 9.

Preferably, the 12 SNPs detailed for the first and second embodiments are used as markers for the detection of introgressed sequence from *S. galapagense*.

According to a preferred embodiment, a plant according to the invention has introgressed sequences from *S. galapagense* at at least one of the 24 loci defined according to the first and second embodiments.

The 12 SNP markers according to the $1^{st}$ or $2^{nd}$ embodiment of the invention are marker loci linked to chromosomal regions or QTL that are involved in or associated with the tolerance or resistance phenotype. The allele of these markers thus indicates whether the sequences surrounding the markers are introgressed from *S. galapagense* or not, introgressed sequences at this locus being correlated to resistance or tolerance to arthropod pest whereas *S. lycopersicum* sequences at this locus are not indicative of resistance or tolerance to arthropod pests.

Regarding the QTL or chromosomal regions marked by the SNPs of the invention, either according to the first or second embodiment, and correlated with the phenotype, a single of this chromosomal region may impart the desired phenotype. According to the invention, it is preferred that at least two and preferably several of the chromosomal regions are present in a plant of the invention, as determined by the SNP markers detailed above. Indeed, the more of these markers are present in a plant of the invention, the more a plant can be expected to have tolerance or resistance to arthropod pest. In addition, the more of the markers are present, the more tolerant are the plants.

The present invention is directed to plant having introgressed sequences from *S. galapagense* at a single locus of the 12 loci or of the 12 alternative loci recited above, however conferring resistance or tolerance to arthropod pest. Preferably, a plant of the invention has introgressed sequences at 2 of the 12 loci or of the 12 alternative loci, and preferably at 3, 4, 5, 6, 8, 10 of the 12 loci or of the 12 alternative loci, or of the 24 loci constituted by the 12 loci and 12 alternative loci.

Insofar as the introgressed sequences from *S. galapagense* conferring resistance to said pest can be marked by the specific alleles of the SNP markers of the invention, a plant of the invention has at least one of the following alleles: allele G of SNP solcap_snp_sl_18619 on chromosome 1, allele C of SNP solcap_snp_sl_12348 on chromosome 1; allele C of SNP EP_1592_LC7762 on chromosome 1, allele T of SNP EE_0301 on chromosome 5, allele G of SNP EE_4363_LC7656 on chromosome 6, allele A of SNP CL016475-0340 on chromosome 9; allele C of SNP EP_0502 on chromosome 9, allele A of SNP EE_4969_LC7529 on chromosome 9, allele T of SNP EE_2332 on chromosome 9, allele C of SNP SL102041269 on chromosome 12, allele A of SNP SGN-U573565_snp665 on chromosome 12 and allele T of SNP EE_0924 on chromosome 12; and preferably at least 2, or 3, 4, 5, 6, 8, 10 of said alleles. The allele combination can be any combination of the above-recited alleles.

Preferred combinations of alleles correspond inter alia to combinations of SNPs found on the same chromosome, for example allele G of SNP solcap_snp_sl_18619, allele C of SNP solcap_snp_sl_12348 and allele C of SNP EP_1592_LC7762 on chromosome 1, or the combination of allele A of SNP CL016475-0340; allele C of SNP EP_0502, allele A of SNP EE_4969_LC7529 and allele T of SNP EE_2332 on chromosome 9, or the combination of allele C of SNP SL10204_1269, allele A of SNP SGN-U573565_snp665 and allele T of SNP EE_0924 on chromosome 12. Other combinations also envisaged in the context of the invention combine at least one allele on each involved chromosomes 1, 5, 6, 9 and 12, for example allele G of SNP solcap_snp_sl_18619 on chromosome 1, allele T of SNP EE_0301 on chromosome 5, allele G of SNP EE_4363_LC7656 on chromosome 6, allele A of SNP CL016475-0340 on chromosome 9 and allele C of SNP SL10204_1269 on chromosome 12, or allele C of SNP solcap_snp_sl_12348 on chromosome 1; allele T of SNP EE_0301 on chromosome 5, allele G of SNP EE_4363_LC7656 on chromosome 6, allele C of SNP EP_0502 on chromosome 9 and allele A of SNP SGN-U573565_snp665 on chromosome 12. According to a preferred embodiment, a plant according to the invention displays introgressed sequences from *S. galapagense*, in at least one of the chromosomes 1, 5, 6, 9 and 12, preferably on at least two of said chromosomes, and preferably at least 3 or 4, or on the 5 chromosomes, at the loci defined above.

According to a preferred embodiment, the *S. lycopersicum* plant of the invention comprises, introgressed in its genome, a chromosomal region or fragment from *S. galapagense*, conferring resistance or tolerance to arthropod pest, especially to *T. absoluta* infestation. Such a chromosomal region or fragment corresponds to or includes:

i. The region delimited by SNPs solcap_snp_sl_59890 and solcap_snp_sl_15339 in chromosome 1 of a plant corresponding to the deposited material, NCIMB accession number 42109; such a region comprises inter alia the following SNPs: solcap_snp_sl_19066, solcap_snp_sl_14042, solcap_snp_sl_18619, solcap_snp_sl_12348, EP_0180_LC7488, EE_2741_LC7681 and EP_0350_LC6805, ii. The region delimited by SNPs solcap_snp_sl_40154 and EP_1592_LC7762 in chromosome 1 of a plant corresponding to the deposited material, NCIMB accession number 42109, iii. The region delimited by SNPs EE_4363_LC7656 and SL10539_786_LC7260 in chromosome 6 of a plant corresponding to the deposited material, NCIMB accession number 42109; such a region comprises inter alia the following SNPs: IL3_2569_LC7566, EE_1008_LC7515, solcap_snp_sl_65595, solcap_snp_sl_32320, solcap_snp_sl_30498, solcap_snp_sl_30511, solcap_snp_sl_31156, SL10187_425, Le004790_246, EP_0572_LC7445, EE_2362, SL10768_133, EE_2996 and solcap_snp_sl_14452, iv. The region delimited by SNPs EP_0489_LC7684 and EE_1452 in chromosome 9 of a plant corresponding to the deposited material, NCIMB accession number 42109; such a region comprises inter alia the following SNPs: SL10004_409_LC7341, IL2_5178, EE_1577_LC7366, EE_1758 LC7427, CL016475-0340, EP 0502, EE_4969_LC7529, EE_2332, IL2_1262, EE_1817_LC6849, EE_3482_LC7808 and EE_5152_LC7199, v. The region delimited by SNPs SL10204_1269 and EE_0924 in chromosome 12 of a plant corresponding to the deposited material, NCIMB accession number 42109; such a region comprises inter alia the SNP SGN-U573565_snp665.

Preferably, a plant according to the invention comprises, introgressed in its genome, at least one chromosomal fragment having *S. galapagense* sequences and corresponding to or comprising one of the chromosomal regions recited above. In a most preferred embodiment, a plant of the invention comprises at least two chromosomal fragments corresponding or comprising at least two of the regions recited above, preferably at least 3 or 4. Most preferably, a plant of the invention comprises, introgressed in its genome, sequences corresponding to or comprising the 5 chromosomal regions defined above.

Said introgressed chromosomal regions from *S. galapagense* are present in the genome of plants of the deposited seeds (deposited at the NCIMB under accession number 42109) and can thus be defined with respect to these plants.

Preferably, a plant of the invention does not comprise any introgression fragment from *S. galapagense* on a chromosome different from chromosomes 1, 5, 6, 9 and 12. Most preferably, in the genome of a plant of the invention, any introgression fragment or introgressed sequences from *S. galapagense* are within one of the following chromosomal segments:

A. The region delimited by SNPs IL3_1821 and EE_4184_LC7793 in chromosome 1 on said plant;
B. The region delimited by SNPs SL10259_474_LC7727 and EP_1027_LC7889 on chromosome 1 of said plant;
C. The region delimited by the telomeric region of the short arm (in north of chromosome 5) and SNP EE_3810_LC7374 on chromosome 5 of said plant;
D. The region delimited by the telomeric region of the long arm (in south of chromosome 6) and SNP solcap_snp_sl_12646 on chromosome 6 of said plant,
E. The region between positions 3 897 900 and 63 642 560, according to the tomato genome sequence build SL2.40, on chromosome 9 of said plant, and
F. The region delimited by the telomeric region of the short arm (in north of chromosome 12) and SNP solcap_snp_sl_1495 on chromosome 12 of said plant.

Therefore, a plant of the invention preferably does not comprise any introgressed sequences from *S. galapagense* donor located outside of the chromosomal segments A to F mentioned above. Moreover, a particularly preferred plant comprises introgressed sequences from *S. galapagense* donor in every segment A to F and does not comprise introgressed sequences outside of these segments.

The introgressed sequences from *S. galapagense* conferring resistance and/or tolerance to arthropod pest according to the present invention are preferably homozygoulsy present in the genome of a plant. Accordingly, such a plant preferably exhibits, on both homologues of chromosome 1, and/or of chromosome 5, and/or of chromosome 6, and/or of chromosome 9 and/or of chromosome 12, introgressed sequences from *S. galapagense* capable of conferring resistance or tolerance to arthropod pest. It must be borne in mind that this thus not necessarily imply that the introgression fragments from *S. galapagense* on both chromosome homologues are identical. Indeed, one of the homologue may comprise only the introgressed sequences necessary and sufficient to confer resistance or tolerance, whereas the other homologue comprises a larger introgression fragment, comprising said sequences in addition to further sequences from *S. galapagense* unrelated to resistance or tolerance. Therefore a plant of the invention is homozygous for at least one of the following alleles: allele G of SNP solcap_snp_sl_18619 on chromosome 1, allele C of SNP solcap_snp_sl_12348 on chromosome 1; allele C of SNP EP 1592 LC7762 on chromosome 1, allele T of SNP EE_0301 on chromosome 5, allele G of SNP EE_4363_LC7656 on chromosome 6, allele A of SNP CL016475-0340 on chromosome 9; allele C of SNP EP_0502 on chromosome 9, allele A of SNP EE_4969_LC7529 on chromosome 9, allele T of SNP EE_2332 on chromosome 9, allele C of SNP SL10204_1269 on chromosome 12, allele A of SNP SGN-U573565_snp665 on chromosome 12 and allele T of SNP EE_0924 on chromosome 12, and preferably homozygous for all these 12 alleles.

Alternatively, according to another embodiment of the present invention, a plant comprises introgressed sequences from *S. galapagense* conferring the desired trait on only one of the two chromosome homologues, i.e. the introgressed sequences conferring resistance or tolerance are present heterozygously in the genome of such a plant.

It is also envisaged that some of the sequences conferring resistance or tolerance, present at any one of the 12 loci or 12 alternative loci defined above, are present homozygously in the genome of a plant of the invention, whereas other introgressed sequences, present at other ones of the 12 loci or alternative loci are present heterozygously in the genome of a plant according to the invention.

The improved tolerance or resistance to arthropod pest is advantageously determined by comparison to a susceptible (commercial) line, for example Rehovot-13 (LYCO2) tomato plants. It is preferably determined on the basis of Percent Leaflet Attacked rating. The present inventors have indeed identified this rating as the best criterion to represent the tolerance or resistance of the plants toward *T. absoluta* attacks. Preferably, this criterion is determined a few days after infestation; a perfectly suitable time-limit is between 3 to 15 days post infestation by the pest, for example 8 days post infestation.

The tolerance or resistance to arthropod pest is for example determined at 8 days after exposure to the pest population, and is considered as "improved" if the difference between the test plant and a susceptible plant is a significant reduction of the PLA. By "significant", it is meant a reduction which is significant from a statistical point of view. Preferably, the significant reduction is a reduction of at least 5% of the PLA for the test plant; preferably, the reduction is of at least 10% or even preferably a reduction by almost 25 or 30%. Plants obtained by the inventors as described in the experimental section display a reduction of at least 50% of the PLA determined at 8 days post infestation.

Therefore, a plant according to the invention preferably displays a PLA score at 8 days post exposure to the pest population which is reduced by at least 30%, preferably at least 50% and most preferably at least 70% with respect to a susceptible commercial *S. lycopersicum* line.

With regard to the experimental conditions for rating the PLA, potential suitable conditions are detailed in the experimental section of the present description. Namely, the PLA is scored preferably in a greenhouse or a nethouse, in presence of an abundant pest population. The climactic conditions in the greenhouse are typical conditions for tomato culture. The PLA score is determined according to the scale defined in Maluf et al. 1997, and detailed in the experimental section.

Other criteria such as LLT (Leaflet Lesion Type) and OPD (Overall Plant Damage) criteria, as defined in the experimental section, can alternatively be used. They are preferably used in addition to the PLA rating, for example to reinforce the confidence on the detected markers.

A plant according to the invention is preferably a plant deriving from a plant grown from the deposited seed under accession number NCIMB 42109, for example a plant derived from one of the deposited seed by one or several backcrosses to a *S. lycopersicum* line. A progeny of a plant obtained from the deposited seed can be identified by one skilled in the art, for example by comparison of the introgression edges. Indeed, the specificity of the location of the introgression edges allows the detection of plants deriving from the deposited plants.

A plant of the invention is also advantageously obtainable by a process comprising an interspecific cross between a *S. galapagense* parent, and a *S. lycopersicum* parent, followed by at least one selfing step and at least two backcrossing steps, whereas the progeny is selected at each stage on the basis of one or more of the alleles of the markers marking the 12 loci; i.e. SNP solcap_snp_sl_18619 on chromosome 1, SNP solcap_snp_sl_12348 on chromosome 1, SNP EP_1592_LC7762 on chromosome 1, SNP EE_0301 on chromosome 5, SNP EE_4363_LC7656 on chromosome 6, SNP CL016475-0340 on chromosome 9, SNP EP 0502 on chromosome 9, SNP EE_4969_LC7529 on chromosome 9, SNP EE_2332 on chromosome 9, SNP SL10204_1269 on chromosome 12, SNP SGN-U573565_snp665 on chromosome 12 and SNP EE_0924 on chromosome 12. Alternatively, the selection may be carried out on the basis of the alleles of the markers marking the 12 alternative loci, i.e. SNP solcap_snp_sl_59890 on chromosome 1, SNP solcap_snp_sl_15339 on chromosome 1, SNP solcap_snp_sl_40154 on chromosome 1, SNP solcap_snp_sl_32320 on chromosome 6, SNP SL10187_425 on chromosome 6, SNP EE_2362 on chromosome 6, SNP EE_2996 on chromosome 6, SNP SL10539_786_LC7260 on chromosome 6, SNP EP_0489_LC7684 on chromosome 9, SNP IL2_5178 on chromosome 9, SNP EE_3482_LC7808 on chromosome 9, and SNP EE_1452 on chromosome 9.

Such a process is described more in detail below with respect to the fourth aspect of the present invention.

In a further embodiment of the invention, the plants as defined are resistant or tolerant to arthropod pest, wherein said arthropods are more specifically insect arthropods, inter alia Lepidoptera or Hemiptera, or acari arthropods.

Particularly preferred arthropods in the context of the present invention are pinworms, and especially the South American pinworm *T. absoluta*.

Alternatively, plants according to the invention are resistant or tolerant to one or more of the following arthropods: aphids, whitefly, thrips, leafminers (Liriomyza), caterpillars (Spodoptera), tomato psyllids, spider mites, rust mites and nematodes, in addition to or in place of resistance to *T. absoluta*. Preferably, a plant of the invention is simultaneously resistant to pinworms, white flies, spider mites, Tomato Russet mites and thrips.

According to a second aspect, the present invention is directed to parts of a plant as defined according to the first aspect of the invention, namely parts of a plant resistant or tolerant to an arthropod pest due to the presence in its genome of introgressed sequences from *S. galapagense*.

A part of a plant is preferably a plant cell; the invention is thus concerned with a plant cell of *S. lycopersicum* comprising in its genome introgressed sequences from *S. galapagense* conferring resistance to said arthropod pest, at one or more of said 12 loci or of said 12 alternative loci.

The different features of the introgressed sequences have been defined in relation with the first aspect of the invention and apply mutatis mutandis to this aspect of the invention. The introgressed sequences are thus preferably chosen from those present in the genome of a plant corresponding to the deposited material TUT115 (NCIMB accession number 42109). Moreover, as detailed extensively in relation to the first aspect, a plant cell of the invention has preferably introgressed sequences from *S. galapagense* at more than one of said loci, preferably at least 2 or 3 loci, preferably at least 5, 8 or 10. Particularly preferred plant cells are those comprising introgressed sequences from *S. galapagense* conferring said resistance or tolerance at the 12 loci defined above, or at the 12 alternative loci, or at the 24 loci.

A plant cell according to this aspect of the invention is thus characterized by the presence in its genome of at least one of the following alleles: allele G of SNP solcap_snp_sl_18619 on chromosome 1, allele C of SNP solcap_snp_sl_12348 on chromosome 1; allele C of SNP EP_1592_LC7762 on chromosome 1, allele T of SNP EE_0301 on chromosome 5, allele G of SNP EE_4363_LC7656 on chromosome 6, allele A of SNP CL016475-0340 on chromosome 9; allele C of SNP EP_0502 on chromosome 9, allele A of SNP EE_4969_LC7529 on chromosome 9, allele T of SNP EE_2332 on chromosome 9, allele C of SNP SL10204_1269 on chromosome 12, allele A of SNP SGN-U573565_snp665 on chromosome 12 and allele T of SNP EE_0924 on chromosome 12.

A plant cell according to the invention may also comprise introgression fragments corresponding to or including one or more of the 5 regions i) to v) defined with respect to the first aspect of the invention.

Preferably, a plant cell of the invention does not comprise introgressed sequences from *S. galapagense* in chromosomes other than chromosomes 1, 5, 6, 9 and 12. More preferably, a plant cell does not comprise introgressed sequences located outside of the chromosomal segments A to F mentioned above, but comprised introgressed sequences from the *S. galapagense* donor within all these 6 segments.

A plant cell of the invention may have the capacity to be regenerated into a whole plant. Alternatively, the invention is also directed to plant cells which are not regenerable, and thus are not capable of giving rise to a whole plant.

According to another embodiment, the plant part is any other part of a plant of the invention, it may be in particular seeds, reproductive material, roots, flowers, fruits, rootstock or scion. Such a part comprises a cell as defined above, i.e. having introgressed sequences from *S. galapagense* capable of conferring resistance or tolerance to arthropod pest to a *S. lycopersicum* plant.

All the preferred embodiments detailed in the preceding section in connection with the first aspect of the invention are also preferred embodiments according to this second aspect of the invention.

The invention is more particularly concerned with seed of a *S. lycopersicum* plant, giving rise when grown up to *S. lycopersicum* plant tolerant or resistant to arthropod pest as defined above, which is preferably a commercial plant also resistant to ToMV (Tomato Mosaic Virus). Such seed are thus 'seed of a plant of the invention', i.e. seed giving rise to a plant of the invention. The invention is also concerned with seed from a plant of the invention, i.e. obtained from such a plant after selfing or crossing, provided however that the plant obtained from said seed is resistant or tolerant to arthropod pest due to introgressed sequences from *S. galapagense* conferring said trait.

According to a third aspect, the present invention is also directed to the use of a tomato plant as detailed according to the first aspect of the invention, i.e. tolerant and/or resistant to arthropod pest, especially to *T. absoluta*, as a breeding partner in a breeding program for obtaining *S. lycopersicum* plants tolerant or resistant to pest arthropods. Indeed, such a tomato plant according to the first aspect harbors in its genome introgressed sequences from *S. galapagense*, conferring said tolerance or resistance. By crossing this plant with susceptible or less resistant plants, it is thus possible to transfer these sequences, conferring the desired phenotype, to the progeny. A plant according to the invention can thus be used as a breeding partner for introgressing sequences conferring the desired phenotype into a *S. lycopersicum* plant or germplasm. The invention is also directed to the same use with plants or seed of TUT115 as deposited at NCIMB under accession number 42109. Said plants are also suitable as introgression partners in a breeding program aiming at conferring the desired phenotype to a *S. lycopersicum* plant or germplasm.

In such a breeding program, the selection of the progeny displaying the desired phenotype, or bearing sequences linked to the desired phenotype, can advantageously be carried out on the basis of the allele of the SNP markers. The progeny is preferably selected on the presence of one or more of the following specific alleles: allele G of SNP solcap_snp_sl_18619 on chromosome 1, allele C of SNP solcap_snp_sl_12348 on chromosome 1; allele C of SNP EP_1592_LC7762 on chromosome 1, allele T of SNP EE_0301 on chromosome 5, allele G of SNP EE_4363_LC7656 on chromosome 6, allele A of SNP CL016475-0340 on chromosome 9; allele C of SNP EP_0502 on chromosome 9, allele A of SNP EE_4969_LC7529 on chromosome 9, allele T of SNP EE_2332 on chromosome 9, allele C of SNP SL10204_1269 on chromosome 12, allele A of SNP SGN-U573565_snp665 on chromosome 12 and allele T of SNP EE_0924 on chromosome 12. The selection can alternatively be made on the basis of the alleles of the 12 alternative SNP markers.

The selection of the progeny having the desired phenotype can also be made on conditions of pest infestation, as disclosed inter alia in example 1 for *T. absoluta*.

A plant according to the invention, or as deposited under accession number NCIMB 42109, is thus particularly valuable in a marker assisted selection for obtaining commercial tomato lines and varieties resistant and/or tolerant to arthropod pest, especially to *T. absoluta*.

The invention is also directed to the use of said plants in a program aiming at identifying, sequencing and/or cloning the genes conferring the desired phenotype, i.e. resistance and/or tolerance to arthropod pest, especially to *T. absoluta*.

Any specific embodiment described for the 1$^{st}$ and 2$^{nd}$ aspects of the invention is also applicable to this aspect of the invention, especially with regard to any combination of SNPs amongst the 12 SNPs of the invention, or amongst the 12 alternative SNPs.

According to a third aspect, the invention also concerns methods for the production of *S. lycopersicum* plants having the desired phenotype, especially commercial plants. Preferably such plants are also resistant to ToMV (Tomato Mosaic Virus).

A method or process for the production of a plant having these features comprises the following steps:
 a) Crossing a plant corresponding to the deposited seeds (NCIMB 42109) and a susceptible or less resistant *S. lycopersicum* plant, in which the desired phenotype is to be imported or improved. Said susceptible plant may possess or not the feature of resistance to ToMV.
 b) Selecting one resistant plant to arthropod pest in the progeny thus obtained, or one plant bearing sequences linked to the desired phenotype; in one embodiment, such a plant is also resistant to ToMV;
 c) Optionally self-pollinating one or several times the resistant plant obtained at step b) and selecting a plant resistant to arthropod pest in the progeny thus obtained; in one embodiment, such a plant is also resistant to ToMV;
 d) Backcrossing the resistant plant selected in step b) or c) with a susceptible *S. lycopersicum* plant (i.e. susceptible to arthropod pest), preferably, such a susceptible plant is resistant to ToMV;
 e) Selecting a plant resistant to arthropod pest and preferably also resistant to ToMV.

Alternatively, the method or process may comprise the following steps:
 a1) Crossing a plant corresponding to the deposited seeds (NCIMB 42109) and a susceptible or less resistant *S. lycopersicum* plant, in which the desired phenotype is to be imported or improved, thus generating the F1 population. Said susceptible plant may possess or not the feature of resistance to ToMV.
 a2) Increasing the F1 hybrid to create F2 population;
 b) Selecting resistant individuals in the progeny thus obtained; in one embodiment, such an individual is also resistant to ToMV.
 c) Optionally self-pollinating one or several times the resistant plant obtained at step b) and selecting a resistant plant in the progeny thus obtained; in one embodiment, such a plant is also resistant to ToMV;
 d) Backcrossing the resistant plant selected in step c) or d) with a susceptible *S. lycopersicum* plant (i.e. susceptible to arthropod pest), preferably, such a susceptible plant is resistant to ToMV;
 e) Selecting a plant resistant to arthropod pest and preferably also resistant to ToMV.

According to another embodiment, it can be selected at steps b), c) and e) either plant tolerant to arthropod pest or resistant to arthropod pest.

The plant selected at step e) is preferably a commercial plant, especially a plant having fruits which weigh at least 25 g, or at least 50 g at full maturity in normal culture conditions.

Preferably, steps d) and e) are repeated at least twice and preferably three times, not necessarily with the same susceptible *S. lycopersicum* plant. Said susceptible *S. lycopersicum* plant is preferably a breeding line.

Resistance to nematode trait may be used in place of or in addition to resistance to ToMV in the processes disclosed above.

The self-pollination and backcrossing steps may be carried out in any order and can be intercalated, for example a backcross can be carried out before and after one or several self-pollinations, and self-pollinations can be envisaged before and after one or several backcrosses.

Moreover, such a method is advantageously carried out by using SNPs markers for one or more of the selections carried out at steps b), c) and/or e) for selecting plants resistant to arthropod pest. The SNP markers are preferably one or more of the 12 SNP markers of the invention, or of the 12 alternative SNP markers, or of a combination of the 24 SNP markers. According to a preferred embodiment, the selection is at least partly made on the basis of the allele of one or more SNP solcap_snp_sl_18619 on chromosome 1, SNP solcap_snp_sl_12348 on chromosome 1; SNP EP_1592_LC7762 on chromosome 1, SNP EE_0301 on chromosome 5, SNP EE_4363_LC7656 on chromosome 6, SNP CL016475-0340 on chromosome 9; SNP EP_0502 on chromosome 9, SNP EE_4969_LC7529 on chromosome 9, SNP EE_2332 on chromosome 9, SNP SL10204_1269 on chromosome 12, SNP SGN-U573565_snp665 on chromosome 12 and SNP EE_0924 on chromosome 12. The selection is preferably carried out by detecting the alleles of at least 2 or 3 of these SNPs, preferably at least 5, 8 or 10, or on the basis of the 12 SNP markers. Preferably, when only a partial set of the 12 markers is used, said set combines SNPs on different chromosomes. Alternatively, partial sets of the 12 markers combine markers which are found in the same region i) to iv) as defined with respect to the first aspect of the invention.

The plant selected at any one of steps b), c) and/or e) is preferably selected on the presence of one or more of the following specific alleles: allele G of SNP solcap_snp_sl_18619 on chromosome 1, allele C of SNP solcap_snp_sl_12348 on chromosome 1; allele C of SNP EP_1592_LC7762 on chromosome 1, allele T of SNP EE_0301 on chromosome 5, allele G of SNP EE_4363_LC7656 on chromosome 6, allele A of SNP CL016475-0340 on chromosome 9; allele C of SNP EP_0502 on chromosome 9, allele A of SNP EE_4969_LC7529 on chromosome 9, allele T of SNP EE_2332 on chromosome 9, allele C of SNP SL10204_1269 on chromosome 12, allele A of SNP SGN-U573565_snp665 on chromosome 12 and allele T of SNP EE_0924 on chromosome 12. The selection can alternatively be made on the basis of the alleles of the 12 alternative SNP markers.

The selection of the progeny having the desired phenotype can also be made on conditions of pest infestation, as disclosed inter alia in example 1 for *T. absoluta*.

The method used for allele detection can be based on any technique allowing the distinction between two different alleles of a SNP, on a specific chromosome.

The invention is also directed to a method or process for obtaining *S. lycopersicum* plants having the desired phenotype, wherein said method comprises the steps of:

a) Making an interspecific cross between a *S. galapagense* plant and a susceptible *S. lycopersicum* plant, b) Selecting one resistant hybrid in the progeny thus obtained or one plant bearing sequences linked to the desired phenotype, c) Optionally self-pollinating one or several times the resistant plant obtained at step b) and selecting a resistant hybrid in the progeny thus obtained;

d) Backcrossing the resistant hybrid selected in step b) or c) with a susceptible *S. lycopersicum* plant (i.e. susceptible to arthropod pest); such a susceptible plant may be resistant to ToMV;

e) Selecting a plant resistant to arthropod pest, f) Self-pollinating the resistant plant obtained at step e), and g) Selecting a plant resistant to pest arthropods and being preferably also resistant to ToMV, wherein steps d) to g) can be repeated and wherein SNPs markers are used in steps b), c), e) and/or g) for selecting plants resistant to arthropod pest, as detailed for the previous method. According to another embodiment, it can be selected plants tolerant to arthropod pest.

The plant selected at step g) is preferably a commercial plant, especially a plant having fruits which weigh at least 25 g, or at least 50 g, at full maturity in normal culture conditions.

The invention also concerns a method wherein steps a) to c) are not carried out and wherein step d) is carried out with a plant obtained from the deposited seed (NCIMB accession number 42109) instead of the resistant hybrid mentioned above in step d).

Resistance to nematode trait may be used in place of or in addition to resistance to ToMV in the processes disclosed above.

All preferred embodiments recited above for the previous method apply mutatis mutandis to this alternative method. Especially, steps d) and e) can be repeated, they are preferably carried out twice, or three times. The same applies to steps f) and g) which are preferably carried out twice, three times or more.

The present invention also concerns a plant obtained or obtainable by such a method. Such a plant is indeed a *S. lycopersicum* plant having the desired phenotype according to the first aspect of the invention and is preferably also resistant to ToMV.

The invention is also directed to a method for obtaining commercial tomato plants, having the desired phenotype, comprising the steps of:

Backcrossing a plant, obtained by germinating the deposited seeds TUT115 (NCIMB accession number 42109), with a *S. lycopersicum* plant, for example a *S. lycopersicum* plant susceptible to arthropod pest; such a *S. lycopersicum* plant may be resistant to ToMV;

Selecting a plant tolerant or resistant to arthropod pest and being preferably also resistant to ToMV.

The selection in the second step is preferably carried out as detailed above for the other methods of the invention. Said selection is preferably carried out on the presence of one or more of the specific alleles of the SNPs of the invention, as found in TUT115.

The plant selected is preferably a commercial plant, especially a plant having fruits which weigh at least 25 g, or at least 50 g, at full maturity in normal culture conditions.

The invention is moreover directed to a method for detecting and/or selecting *S. lycopersicum* plants having introgressed sequences from *S. galapagense* conferring resistance to arthropod pest, on the basis of the allele detection of at least one SNP chosen amongst the group of SNPs comprising SNP solcap_snp_sl_18619 on chromosome 1, SNP solcap_snp_sl_12348 on chromosome 1; SNP EP_1592_LC7762 on chromosome 1, SNP EE_0301 on chromosome 5, SNP EE_4363_LC7656 on chromosome 6, SNP CL016475-0340 on chromosome 9; SNP EP_0502 on chromosome 9, SNP EE_4969_LC7529 on chromosome 9, SNP EE_2332 on chromosome 9, SNP SL102041269 on chromosome 12, SNP SGN-U573565_snp665 on chromosome 12 and SNP EE_0924 on chromosome 12. Preferably, tolerant or resistant plants are selected if at least one of the following markers is detected: allele G of SNP solcap_snp_sl_18619, allele C of SNP solcap_snp_sl_12348; allele C of SNP EP_1592_LC7762, allele T of SNP EE_0301, allele G of SNP EE_4363_LC7656, allele A of SNP CL016475-0340; allele C of SNP EP_0502, allele A of SNP EE_4969_LC7529, allele T of SNP EE_2332, allele C of SNP SL10204_1269, allele A of SNP SGN-U573565_snp665 and allele T of SNP EE_0924, in a genetic material sample of the plant to be selected. According to a preferred embodiment, the allele of interest which is detected is present homozygously in the selected plant, i.e. no other allele of said SNP is present.

According to a particularly preferred embodiment, the selection is thus made on the simultaneous presence of the 12 following alleles: allele G of SNP solcap_snp_sl_18619, allele C of SNP solcap_snp_µl_12348; allele C of SNP EP_1592_LC7762, allele T of SNP EE_0301, allele G of SNP EE_4363_LC7656, allele A of SNP CL016475-0340; allele C of SNP EP_0502, allele A of SNP EE_4969_LC7529, allele T of SNP EE_2332, allele C of SNP SL10204_1269, allele A of SNP SGN-U573565_snp665 and allele T of SNP EE_0924, and the concomitant absence of the following alleles: allele T of SNP solcap_snp_sl_18619, allele T of SNP solcap_snp_sl_12348; allele T of SNP EP_1592_LC7762, allele G of SNP EE_0301, allele T of SNP EE_4363_LC7656, allele G of SNP CL016475-0340; allele A of SNP EP_0502, allele G of SNP EE_4969_LC7529, allele C of SNP EE_2332, allele T of SNP SL10204_1269, allele T of SNP SGN-U573565_snp665 and allele C of SNP EE_0924.

Such a combination of alleles is to be found in plants grown up from to the deposited seed. Any specific combination of alleles described in the other parts of the application is also applicable to the present aspect of the invention.

In addition to introgression of the sequences conferring resistance or tolerance to arthropod pest, as detailed in the methods of the invention, said sequences can also be introduced into *S. lycopersicum* background by genetic engineering in order to obtain a commercial *S. lycopersicum* plant resistant or tolerant to said pest. The identification and cloning of the introgressed sequences from *S. galapagense* conferring the desired phenotype, inter alia from the deposit, are routine for the skilled person.

According to a further aspect, the present invention is also directed to hybrid plant of *S. lycopersicum*, obtainable by crossing a tolerant or resistant plant according to the first aspect of the invention, or a tolerant or resistant plant obtainable by the method disclosed according to the fourth aspect, with a plant of *S. lycopersicum*, for example a plant susceptible to arthropod pest, or a plant with a different level of resistance or tolerance to arthropod pest.

A particularly preferred hybrid *S. lycopersicum* plant, is a plant which displays a cytoplasmic male sterility, or any other trait or phenotype of agronomical interest.

LEGEND OF FIGURES

Figure 5:
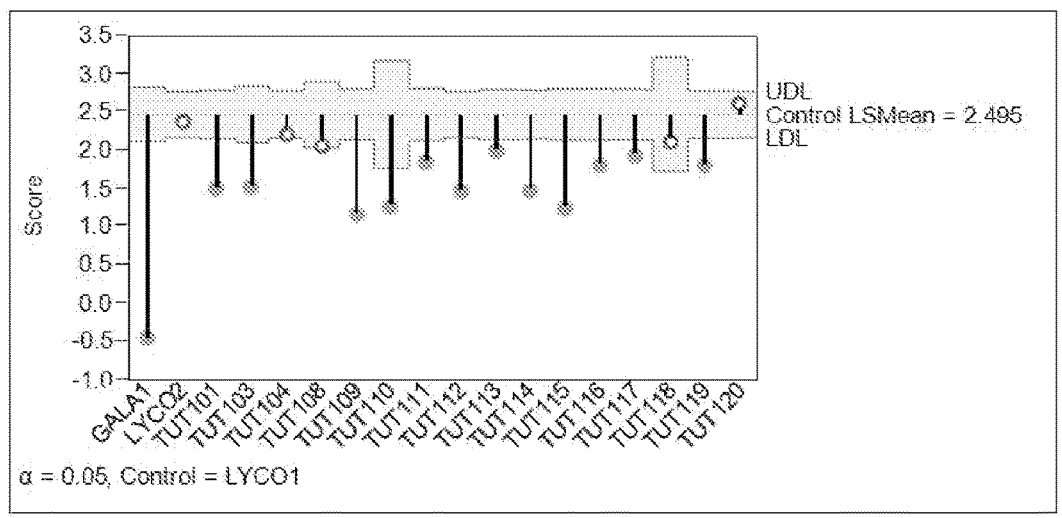

FIG. 5: tomato resistance against spider mites. Feeding damage was analyzed using a Hsu-Dunett LSMeans Difference test for significance. Solid dots indicate if an individual RIL line is significantly different compared to recurrent parent LYCO1. UDL=Upper Decision Limit, LDL=Lower Decision Limit. The grey area emphasizes decision limits indicating a significant difference compared to the LYCO1 LSMean.

Figure 6:
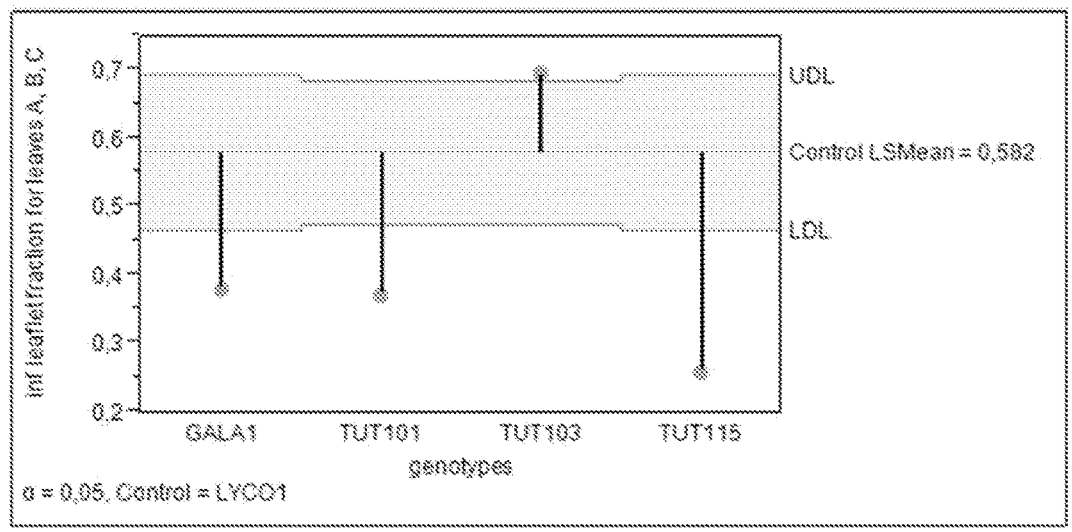

FIG. 6: tomato resistance against thrips. Feeding damage was analyzed using a Hsu-Dunett LSMeans Difference test for significance. Solid dots indicate if an individual RIL line is significantly different compared to recurrent parent LYCO1. UDL=Upper Decision Limit, LDL=Lower Decision Limit. The grey area emphasizes decision limits indicating a significant difference compared to the LYCO1 LSMean.

EXPERIMENTAL SECTION

Example 1

Test of a Possible Source of Resistance to *T. absoluta*

As a starting point of the realization of the invention, the present inventors have conducted several experiments to screen for tomato pinworm resistance amongst several tomato species. As of today, *S. galapagense* has not been identified as a possible source of resistance to *T. absoluta*.
Materials and Methods:
Tomato Germplasm Rearing Tomato germplasm was sown and reared in nursery trays (187 holes of 1.5"/tray). Seedlings having 3-4 true leaves were transplanted into 1 L pots containing soil mixture of peat and volcano soil (2:1). Plants were transferred to an insect free greenhouse for further development. Plants were regularly watered and fertilizer was added (6:6:6 NPK+ micro elements). Temperatures varied between day and night and over seasons: namely 26° C. at day and 17° C. at night in winter, and 27° C. at day and 23° C. at night in summer. No insecticides were applied, and after three weeks plants were treated with the fungicide PROPAMOCARB-HCL. Plants having at least 6 true leaves were used for experiments, these plants were approximately 6 weeks old and 30-45 cm of height.

Germplasms tested are mentioned in table 1:

TABLE 1

| Name | Species |
|---|---|
| LYCO3 | S. lycopersicum |
| LYCO4 | S. lycopersicum |
| LYCO5 | S. lycopersicum |
| LYCO1 | S. lycopersicum |
| LYCO6 | S. lycopersicum |
| LYCO2 (Rehovot-13) | S. lycopersicum |
| HABRO1 | S. habrochaites |
| PENN1 | S. pennellii |
| PERU1 | S. peruvianum |
| HABRO2 | S. habrochaites |
| PIMP1 | S. pimpinellifolium |
| NEORI | S. neorickii |
| PENN2 | S. pennellii |
| PERU2 | S. peruvianum |
| CHMIE1 | S. chmielewskii |
| GALA1 | S. cheesmaniae or S. galapagense |
| HABRO3 | S. habrochaites |
| HABRO4 | S. habrochaites glabratum |
| ARCA1 | S. arcanum |
| PERU3 | S. peruvianum |
| CHMIE2 | S. chmielewskii |

South American Tomato Pinworm Rearing

The South American tomato pinworm population is reared on LYCO2 tomato plants. Plants having at least 6 true leaves were placed in an insect cage (45*45*90 cm; 150 mesh gauze), to which adult pinworms were added. Pinworm adults were collected from infested commercial greenhouse tomato plants. Insects were reared at approximately 25° C. and under 16 hr:8 hr (L:D) (TLD 840 36 W Philips) light conditions. Under these growing conditions the pest life cycle lasts approximately 28 days. For transferring adult tomato pinworms an insect vacuum collector was used.
Tomato Pinworm Oviposition Experiment: Multiple Choice Experiment A selection of 15 different genotypes (see also table 1) were tested for differences in oviposition attractiveness for pinworm females. One plant originating from one genotype was randomly placed in an insect cage (45*45*90 cm; 150 mesh gauze). Experimental plants were exposed to 100 adult moths. Two days post infestation (2 dpi) the total number of eggs per leaves present per genotype were scored (24-26° C., 50-70% RH; 8 hr darkness and 16 hr light (Philips reflex TLD 840 36 W)).
Tomato Pinworm Oviposition Experiment: Three Choice Experiment Differences in pinworm oviposition behavior between three genotypes, i.e. LYCO2, LYCO1, and GALA1 (see table 1), were studied. Plants were positioned in an insect cage (45*45*90 cm; 150 mesh gauze), and were exposed to 50 adult moths. Three days post infestation (3 dpi) the number of eggs laid on the first fully developed leaf per genotype were counted (24-26° C., 50-70% RH; 8 hr darkness and 16 hr light (Philips reflex TLD 840 36 W)).
Pinworm Feeding Behavior Experiment Pinworm larval feeding behavior was studied by exposing a selection of tomato genotypes to adult moths in a choice set-up. Plants were positioned in an insect cage (45*45*90 cm; 150 mesh gauze). One cage contained 15 randomly placed individual plants from different germplasm, the experiment consisted out of two replicates. Per replicate the genotypes under testing (see also table 1) were exposed to 100 adult moths. Seven days post infestation the exact number of mines per leaf were counted, since number of mines are indicative for feeding attractiveness by the pinworm larvae. A mine is the space created in leaf tissue between the epidermal layers by herbivore feeding (24-26° C., 50-70% RH; 8 hr darkness and 16 hr light (Philips reflex TLD 840 36 W)).

Identification of the Resistant Recombinant Inbred Lines Developed from GALA1 and LYCO1

Greenhouse

Experiments were conducted in a plastic greenhouse of approximately 300 m². Inside the greenhouse LYCO2 tomato plants were used for building up a tomato pinworm population, for this end on regular basis new LYCO2 plants obtained from the nursery were transplanted in the greenhouse in 15 L pots filled with clean volcano soil. LYCO2 tomato plants were grown on both long outer rows of the greenhouse.

The internal rows were divided into 14 different sections (plots) with 16 pots each (15 L), in between plots also some LYCO2 tomato plants were positioned.

Plant Preparation Used for Identification Experiments:

All plants that were used in the choice experiment were sown and reared in the nursery in trays (187 holes of 1.5"/tray), without the application of insecticides. Seedlings having 3-4 true leaves were transplanted into 1 L pots containing soil mixture of peat and volcano soil (2:1). Plants were transferred to an insect free greenhouse for further development until they reached at least 6 true leaves up to 10 true leaves. This variation in number of true leaves was caused by differences in plant growth between tomato germplasm. Plants were supported by bamboo sticks using plastic clips.

Set-Up of the Greenhouse Experiments:

When tomato pinworms reared on LYCO2 plants were abundantly present in the greenhouse, tomato germplasm ready for testing were transferred into the greenhouse. Selected plants for testing were roughly one meter of height (+/− BBCH-18: 8 true leaves: 7 weeks after sowing) (Zadoks et al., 1974). Plants were directly positioned with their 1 L plastic pots into the 15 L pots, and a drip irrigation dropper was positioned in the 1 L pot. The tomato plants were placed in the greenhouse in a plot design with 7 experimental repetitions. Within each plot plants were positioned randomly. Temperatures varied between 17° C. at night and 40° C. during the day. The total RIL population screen experiment was divided in sub-experiments by plantation date.

From each plant in BBCH-18, 3 consecutive fully developed leaves positioned in the upper third part of the plant were tagged. Three days after positioning in the greenhouse, eggs were counted on all tagged leaves. Approximately 8 and 13 days after exposure to the pinworm population in the greenhouse, the Leaflet Lesion Type (LLT), the Percent Leaflet Attacked (PLA) were scored per prior tagged leaflets, and Overall Plant Damage (OPD) was noticed (see: Maluf et al., 1997, table 1). Analysis of means using a Dunnett's method. For this, the susceptible recurrent parent of the RIL population, LYCO1, was used as a control.

TABLE 2

Indexing system used to score the parameters Leaflet Lesion Type (LLT), Overall Plant Damage (OPD) and Percent Leaflets Attacked (PLA) in plants infested by the pinworm.

LLT (= Leaflet Lesion Type) Scores:

0 = no lesion.
1 = lesions small, rare.
2 = small to medium-size lesions, usually towards the leaflet borders.
3 = medium to large-size lesions, coalescent; foliar borders deformed.
4 = large-size lesions, coalescent; leaflets deformed.
5 = whole leaflet surface lesioned.

OPD (= Overall Plant Damage) Scores:

0 = no leaf damage.
1 = up to 5% total leaf area damaged; small, non-coalescent lesions.
2 = >5% up to 20% total leaf area damaged; small, non-coalescent lesions.
3 = >20% to 50% total leaf area damaged; medium to large-size lesions.
4 = >50% up to 80% total leaf area damaged; lesions numerous, large, coalescent.
5 = >80% to 100% total leaf area damaged.

PLA (= Percent Leaflets Attacked) Scores:

0 = no leaflets attacked.
1 = 0% to 5% leaflets attacked.
2 = 5% to 20% leaflets attacked.
3 = 20% to 50% leaflets attacked.
4 = 50% to 80% leaflets attacked.
5 = 80% to 100% leaflets attacked.

Results

1/ Pinworm Oviposition Behaviour 1.1/ Multiple-Choice Experiment

Pinworm oviposition preferences were studied under climatized lab-conditions. For each tested genotype one plant was positioned in an experimental cage. Plants were approximately of the same height, while number of leaves ranged between 6 and 11. Plants were exposed to 100 adult moths for 2 days, after which number of eggs per leaf per plant were scored. Per tested genotype the average number of eggs per leaf were calculated.

Figure 1:
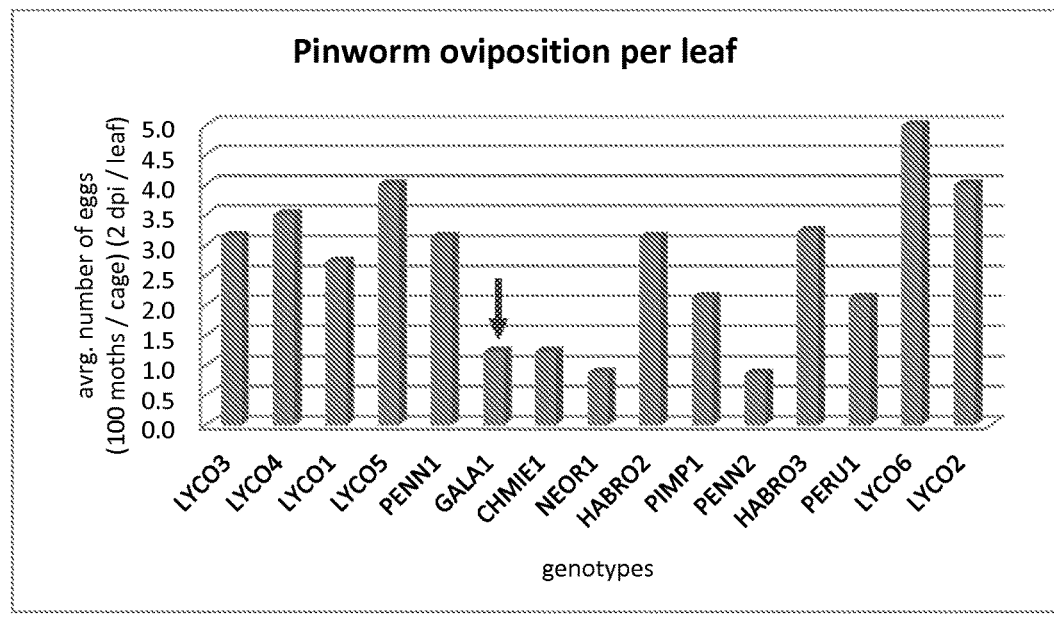
FIG. 1 illustrates the Pinworm oviposition per leaf, for different germplasms in a multiple choice experiment. The pinworm under test is *T. absoluta*.

Results are presented in FIG. 1. As can be seen from this figure, GALA1 presents very low number of eggs per leaf in this type of experiment.

1.2/ Three-Choice Experiment:

Different tomato genotypes were tested in a choice experiment for oviposition preferences by the pinworm. Plants were positioned in an experimental cage (one plant per genotype) under controlled lab-conditions. Plants were approximately of the same height, while number of leaves ranged between 7 and 11. Plants were exposed to 50 adult moths for 3 days. Three days post infestation the exact number of eggs on the first fully developed leaf per plant was counted.

Figure 2:
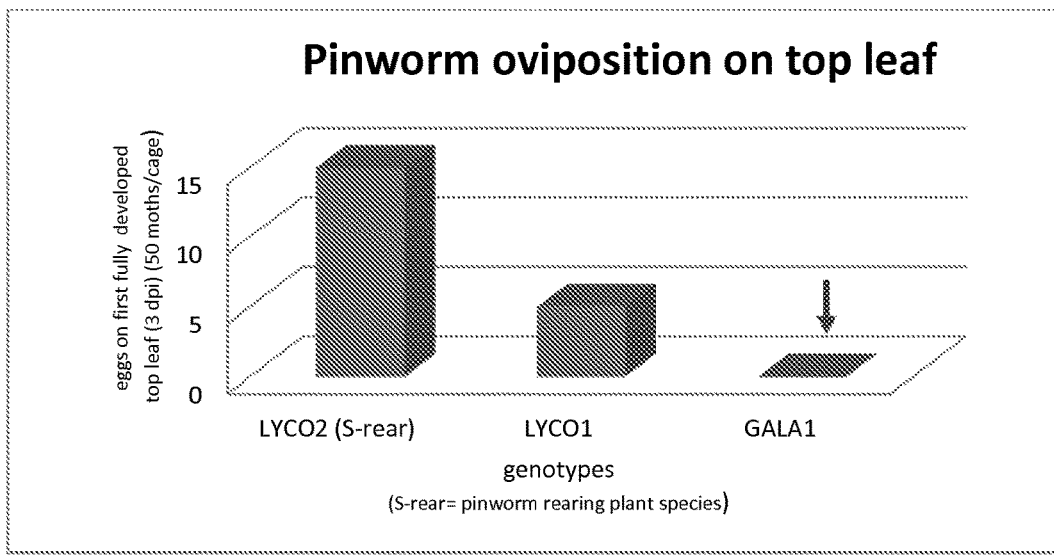
FIG. 2 illustrates the Pinworm oviposition per leaf, for the rearing variety for *T. absoluta*, the recurrent line LYCO1 and the germplasm GALA1, in a three choice experiment. The pinworm under test is *T. absoluta*.

Results are presented in FIG. 2, which illustrates that GALA1 is far less susceptible to pinworm feeding than the variety LYCO2 on which the pinworm was reared, and LYCO1.

2/ Pinworm Feeding Behaviour

Pinworm larval feeding behaviour was studied by exposing tomato genotypes to 100 adult moths in a choice experiment. Tested tomato genotypes were positioned in a cage under climatized lab-conditions (two replicates with one plant per genotype).

Plants were approximately of the same height, while number of leaves ranged between 6 and 11. At 7 dpi the exact numbers of mines per leaf were counted.

Figure 3:
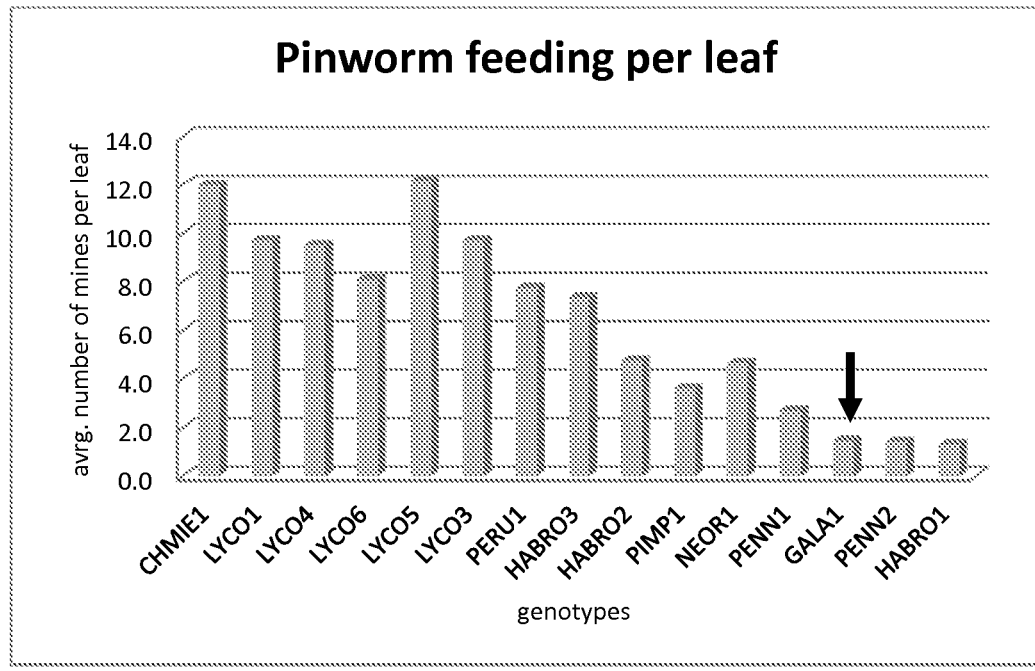
FIG. 3 illustrates the pinworm feeding per leaf. The pinworm under test is *T. absoluta*.

Results are presented in FIG. 3. This figure illustrates that GALA1 is far less susceptible to pinworm feeding than most of the tested other germplasms.

Conclusion:

In the conducted tests, the present inventors demonstrated a level of resistance for several genotypes against the pinworm. Based on these results, the inventors selected GALA1 as the most suitable candidate for further experiments.

3/ Identification of the Resistant RIL-Varieties Developed from GALA1 and LYCO1

Aim:

In this experiment the inventors studied direct and indirect life cycle parameters like oviposition and feeding of the pinworm on donor GALA1 (*L. galapagense*), recurrent parent LYCO1 (*L. esculentum*), the rearing variety for the pinworm, i.e. LYCO2, and the individual RIL-lines.

Results:

The RIL population created with donor GALA1 and recurrent parent LYCO1, was screened for resistance against the tomato pinworm.

More specifically, the used RIL population was an interspecific population derived from a cross between *S. lycopersicum* (inbred cultivar LYCO1) and *S. galapagense* GALA1. LYCO1 was verified as susceptible to South American Pinworm. This population consisted of F8 Recombinant Inbred Lines (RILs) developed by Single Seed Descent.

RIL lines per sub-experiment with significant higher levels of resistance than their recurrent parent, LYCO1, are listed below in table 3. Means for distinct parameters from RIL's were statistically compared with the mean of the recurrent parent per plantation date. A ranking of only the significantly different resistant RIL-lines per parameter was performed by normalization using the recurrent parent as the denominator (if the normalized mean is <1, the plant is resistant; if the normalized mean is 1, the plant is susceptible). Within this invention the inventors characterized as most robust resistance RIL lines TUT101, TUT103, TUT110 and TUT117. RIL-lines TUT115, TUT110 and TUT111 demonstrated strongest immediate, at PLA1, resistance against oviposition.

and OPD. TUT115 has been deposited by Hazera Genetics Ltd, Berurim, M. P. Shikmim 79837, Israel, with the NCIMB (NCIMB Ltd, Ferguson Building, Craibstone Estate, Bucksburn, Aberdeen AB21 9YA, United Kingdom), on 11 Feb. 2013, under accession number NCIMB 42109.

Phenotypic Information Based on PLA:

Phenotypic information (based on PLA) shows that both line TUT115 and TUT101 display a significant reduction in leaves affected by *T. absoluta*. Line TUT115 is at the level of the donor and line TUT101 only at $\frac{1}{5}^{th}$ of the recurrent (=susceptible) parent.

Genotypic information (see example 2) show no difference between line TUT115 and TUT101.

| PLA adjusted | |
|---|---|
| Recurrent parent LYCO1 | 53% |
| Donor GALA1 | 2.50% |
| TUT115 | 0% |
| TUT101 | 11% |

4/ Validation Experiments Promising RIL-Leads

In this experiment, the inventors validated in a growth-chamber the earlier detected resistance levels of promising RIL-leads from the greenhouse screen.

Promising resistant tomato RIL-lines, the donor and the recurrent parent were reared as described in example 1 (see par. Tomato germplasm rearing from Materials and Methods). In one experimental cage (90 cm*90 cm*130 cm (H*W*L); 150 mesh gauze) 11 plants (6-10 true leaves, 5-8 weeks old, height 30-60 cm) were tested for resistance.

One experimental cage contained 4 RIL lines for testing (i.e TUT101, TUT110, TUT115 and TUT103) in replica, 2 recurrent parent plants and 1 donor plant. From each plant 3 consecutive fully developed leaves positioned in the upper third part of the plant were tagged. Plants were infested by introducing 100 adult tomato pinworms per experimental cage. One experiment contained 8 experimental cages (24-26° C.; 50-70% RH; 8 hr darkness: 16 hr light (Philips reflex TLD 840 36 W).

TABLE 3

Identified RIL's with a higher resistance level than the recurrent parent (LYCO1). Displayed are only the RIL's with a significant lower mean score for a given parameter at two time points per sub-experiment (n = number of plants).

| PLA1 | n | mean (RIL)/ mean (LYCO1) | PLA2 | n | mean (RIL)/ mean (LYCO1) | LLT2 | n | mean (RIL)/ mean (LYCO1) | OPD2 | n | mean (RIL)/ mean (LYCO1) |
|---|---|---|---|---|---|---|---|---|---|---|---|
| TUT115 | 7 | 0.09 | TUT101 | 8 | 0.75 | TUT101 | 8 | 0.66 | TUT101 | 8 | 0.44 |
| TUT110 | 7 | 0.42 | TUT110 | 7 | 0.76 | TUT120 | 7 | 0.75 | TUT103 | 7 | 0.54 |
| TUT111 | 8 | 0.48 | TUT117 | 7 | 0.85 | TUT111 | 8 | 0.75 | TUT104 | 7 | 0.62 |
| TUT114 | 7 | 0.61 | TUT119 | 7 | 0.92 | TUT112 | 7 | 0.75 | TUT110 | 6 | 0.75 |
| TUT108 | 8 | 0.61 | | | | TUT113 | 8 | 0.75 | TUT111 | 8 | 0.75 |
| TUT101 | 8 | 0.61 | | | | TUT115 | 7 | 0.75 | TUT114 | 7 | 0.79 |
| TUT118 | 7 | 0.81 | | | | TUT116 | 7 | 0.75 | | | |
| | | | | | | TUT103 | 7 | 0.78 | | | |
| | | | | | | TUT109 | 8 | 0.78 | | | |
| | | | | | | TUT110 | 6 | 0.79 | | | |

Observed resistance could be seen as one trait or as a combination of traits that influence the performance of the pest and or the damage caused by the pest. Several underlying plant-characteristics might explain the observed non-feeding-preference.

Therefore, the inventors conclude that they have identified resistance (comprising inter alia non-feeding-preference) indicated by PLA and to a lower extend also by LLT Three days after tomato pinworm introduction, eggs were counted on all tagged leaves. Approximately 8 and 13 days after introducing the adult moths, the Leaflet Lesion Type (LLT), the Percent Leaflet Attacked (PLA), and Overall Leaf Damage (OLD) were scored per prior tagged leaflets, and Overall Plant Damage (OPD) was noticed. Test parameters were analyzed for significant differences with an Oneway Analysis of means using a Dunnett's method. For this, the susceptible recurrent parent of the RIL population, LYCO1, was used as a control. (See table 2 for the indexing system).

Results

In this choice experiment selected RILs were compared against the recurrent parent LYCO1. Means from individual lines were adjusted by introducing a cage-effect into the linear model. Individual lines were compared using the Tukey Kramer test.

The analysis confirmed for OPD2, PLA 1 & PLA 2 the earlier obtained observations in the RIL selection experiment (section 3/). Recurrent parent LYCO1 is significantly more susceptible compared to wild type donor GALA1, as well as individual RIL lines TUT101 and TUT115. Regarding parameter OPD1, RIL line TUT110 is not different compared to LYCO1, and for both PLA measurements (i.e. timepoints one and two) TUT103 does not significantly differ from LYCO1.

For measured parameters OLD1, LLT2 and the actual egg counting numbers, the obtained data for the RIL-lines indicate no significant differences compared with the recurrent parent. Donor GALA1, did also not differ significantly from the validated RIL lines and LYCO1 for the actual egg-counts, but did show more significant resistance for the OLD and LLT measurements. This clearly shows the difficulty one may encounter to identify the appropriate parameter to measure the resistance.

TABLE 4

Tested parameters that indicate significant differences with LYCO1 (Oneway Analysis of means using a Dunett's method; $P < 0.05$)

| Line | OPD 2 | PLA 1 | PLA 2 | OLD | LTT |
|---|---|---|---|---|---|
| TUT101 | + | + | + | − | − |
| TUT110 | − | + | + | − | − |
| TUT115 | + | + | + | − | − |
| TUT103 | + | − | − | − | − |
| GALA1 | + | + | + | + | + |

Example 2

Development of Molecular Markers and Identification of the Underlying Genetic

Materials and Methods

Plant Materials and DNA Extraction:

The discovery population for the experiment was an interspecific population derived from a cross between *S. lycopersicum* (inbred cultivar LYCO1) and *S. galapagense* GALA1. LYCO1 was verified as susceptible to South American Pinworm, and GALA1 was identified as resistant to South American Pinworm (example 1) This population consisted of F8 Recombinant Inbred Lines (RILs) developed by Single Seed Descent.

Genomic DNA from tomato leaves was extracted using Qiagen DNeasy plant DNA extraction kit.

SNP Genotyping

A set of 737-SNPs combination was selected based on their allelic variation and evenly spaced along the genome. High-throughput SNP genotyping was carried out with the GoldenGate assays and the BeadXpress reader from Illumina. The genotypes (of the RILs and of the two parental lines) were screened with 384 markers in a single plate. SNP genotyping data was scored using the Illumina GenomeStudio genotyping software with a no-call threshold of 0.25.

Illumina GoldenGate Technology Details

A SNP set was designed for the Illumina GoldenGate assay, which used locus and allele-specific oligos with cy3/cy5 labeling to detect SNP alleles at each locus. These custom Oligo Pool Assay (OPA) sets were then run on the Illumina BeadXpress Reader as 384-plex VeraCode assays. Veracode uses cylinder microbeads with an internal barcode to differentiate bead types which correspond to different SNP loci (384 bead types are used for a 384-plex SNP set), and each microbead was coated with oligos that contain a unique address that hybridizes with the labeled products. During scanning on the BeadXpress Reader, the beads were aligned in a groove plate, and the bead codes and cy3/cy5 signal intensities were measured across replicated sets of beads to assign the SNP alleles. This procedure allowed a rapid, high-quality SNP calling of 96 samples by 384 SNPs without requiring fixed arrays. The GenomeStudio software from Illumina was used for clustering alleles based on the ratio of the cy3/cy5 signal intensities to call the three genotype classes.

310 SNPs were retained as technically valid and polymorphic markers.

Selection of Polymorphic SNPs

SNPs with call rate below 70% or with no polymorphism between donor and recurrent parents were removed from the analysis, resulting in 310 SNPs for further analysis.

Identifying Markers Significantly Linked with Each Phenotypic Trait

Phenotypic Data

Phenotypic data was collected as described in example 1. In short, the resistance phenotype was identified by several measurement methods: 1) percent leaflet attacked (PLA), 2) leaflet lesion type (LLT) and 3) overall plant damage (OPD) {Maluf, 1997}. Each was measured in two time points. The first PLA measurement was the only one that distributes normally, and therefore it was used for marker identification. Information from the two other measurement methods was used to reinforce the confidence in the associated markers.

Heritability

Broad sense heritability was calculated by dividing the sum of squares of the difference from the mean for all RILs by the total sum of squares.

Phenotypic Data Normalization

Since plants were grown and measured in different dates, normalization was required. Phenotypic data was normalized using a mixed linear model {Zar, 2010}, including planting and measurement date as fixed effects. The adjusted means from the model were used as input for the association study described below.

Association

The genotyping information described in the SNP genotyping section, and the adjusted mean of the phenotypic measurements were used as input to association mapping via one way ANOVA, using R {Broman 2009}. Each marker was considered independently in order to detect significant markers. The significant markers were then analyzed in the same model in order to retrieve their combined $R^2$.

LD Analysis and Haplotype-Blocks Identification

In order to define the boundaries of the resistant-donor genomic segments that were introduced into the RIL population (i.e. segments that were introduced to the recurrent background as a single continuous segment with almost no recombination in the population) the inventors investigated the LD (Linkage Disequilibrium) patterns in the RIL population. Pairwise LD estimation for all marker combinations in each chromosome was conducted using Haploview software {Barrett, 2005}. Pairwise LD was measured as the D' statistic {Lewontin, 1964}. Haplotype-blocks were defined using the "solid-spine" option which was defined as a "spine" of strong LD running from one marker to its adjacent markers in the LD chart, meaning that the first and last markers in a block were in strong LD with all intermediate markers although the intermediate markers were not necessarily in LD with each other.

Results

Some RILs were phenotyped and genotyped using 310 polymorphic SNPs. The SNPs were physically mapped to the tomato genome version 2.1 {Bombarely, 2011} and then adjusted to the tomato genome version 2.40.

The broad sense heritability of the resistance to South America tomato pinworm as defined by the first PLA measurement is 0.6. This means 60% of the trait as observed by this experiment can be explained by genetic factors, either additive or dominant.

Association analysis identified a set of markers significantly linked to resistance to South America tomato pinworm as defined by the first PLA measurement. The list of associated markers and their significance are summarized in table 5. This table comprises all significant markers resulting from the analysis of the phenotypic data, associated to SNP markers by an ANOVA model. The combined $R^2$ of the listed markers amounts to 0.55, meaning all markers together explain 55% of observed phenotypic variance. The allelic state of the significant markers is identical in the resistant parent and the most resistant RIL, namely TUT115, as described in example 1.

TABLE 5

| Chromosome | position (genome version 2.40) | SNP | P value[a] | significant in additional measurements (with p-value) | Haplotype block[b] |
|---|---|---|---|---|---|
| 1 | 68 232 900 | solcap_snp_sl_18619 | 0.02 | | |
| 1 | 72 528 600 | solcap_snp_sl_12348 | 0.01 | LLT (0.01) | |
| 1 | 83 766 400 | EP_1592_LC7762 | 0.001 | | |
| 5 | 3 636 270 | EE_0301 | 0.02 | LLT (0.01) | |
| 6 | 166 755 | EE_4363_LC7656 | 0.03 | | |
| 9 | 22 094 800 | CL016475-0340 | 0.04 | LLT2 (0.01), PLA2 (0.01) | 1 |
| 9 | 41 847 000 | EP_0502 | 0.04 | LLT2 (0.01), PLA2 (0.01) | 1 |
| 9 | 49 173 600 | EE_4969_LC7529 | 0.04 | LLT2 (0.01), PLA2 (0.01) | 1 |
| 9 | 54 692 600 | EE_2332 | 0.04 | LLT2 (0.01), PLA2 (0.01) | 1 |
| 12 | 124 598 | SL10204_1269 | 0.05 | LLT2 (0.05), PLA2 (0.006) | |
| 12 | 155 493 | SGN-U573565_snp665 | 0.05 | LLT2 (0.05), PLA2 (0.006) | |
| 12 | 1 166 000 | EE_0924 | 0.01 | OPD (0.03), LLT2 (0.015), OPD2 (0.03), PLA2 (0.006) | |

[a]P-value The probability to obtain the result by chance. P value below 0.05 is considered significant.
[b]Haplotype Block - Adjacent markers with a low recombination rate between them belong to the same haplotype block. Markers from the same chromosome and haplotype block are marked by a gray background.

In addition, the occurrence of several markers in one haplotype was investigated. Several markers were found adjacent to each other on the same chromosome, suggesting a low recombination rate between them. Therefore they were inherited as a single haplotype block. In table 5, the relevant haplotype block (if available) is listed for each SNP.

In table 6 is given the allele of the 12 markers, for different resistant lines, as identified in example 1.

TABLE 6

| Chromosome | Marker | TUT101 | TUT110 | TUT115 | TUT103 | T3 | T6 |
|---|---|---|---|---|---|---|---|
| 1 | solcap_snp_sl_18619 | G/G | G/G | G/G | T/T | T/T | G/G |
| 1 | solcap_snp_sl_12348 | C/C | T/T | C/C | C/C | T/T | C/C |
| 1 | EP_1592_LC7762 | * | * | C/C | * | T/T | C/C |
| 5 | EE_0301 | T/T | G/G | T/T | G/G | G/G | T/T |
| 6 | EE_4363_LC7656 | G/G | G/G | G/G | T/T | T/T | G/G |
| 9 | CL016475-0340 | A/A | G/G | A/A | G/G | G/G | A/A |
| 9 | EP_0502 | C/C | A/A | C/C | A/A | A/A | C/C |
| 9 | EE_4969_LC7529 | A/A | G/G | A/A | G/G | G/G | A/A |
| 9 | EE_2332 | T/T | C/C | T/T | C/C | C/C | T/T |

TABLE 6-continued

| Chromosome | Marker | TUT101 | TUT110 | TUT115 | TUT103 | T3 | T6 |
|---|---|---|---|---|---|---|---|
| 12 | SL10204_1269 | C/C | C/C | C/C | T/T | T/T | C/C |
| 12 | SGN-U573565_snp665 | A/A | A/A | A/A | T/T | T/T | A/A |
| 12 | EE_0924 | T/T | T/T | T/T | C/C | C/C | T/T |

* neither T, nor C was detected by the assay.

The genotype of all the 310 SNP markers used in this study is given for TUT115 in table 7. In the last column of table 6, "1" means that the allele of the SNP marker corresponds to the resistant donor parent, wherein "2" means that the allele of the SNP marker corresponds to the recurrent susceptible parent. The SNPs with an asterisk (*) and in italics are the 12 SNP markers mentioned in tables 5 and 6.

The SNP in bold with the symbol "Δ" indicate the <<edge>>, in terms of SNPs, of the introgression fragment, start ("Δs") or end ("Δe").

The chromosome position is by reference to the tomato genome version 2.40.

TABLE 7

| SNP | TUT115 | LYCO1 | GALA1 | CHROMOSOME | POSITION | Donor/recurrent |
|---|---|---|---|---|---|---|
| EE_4663_LC7672 | T/T | T/T | C/C | 1 | 1558580 | 2 |
| EE_2169_LC7254 | A/A | A/A | G/G | 1 | 2204620 | 2 |
| IL3_1821 | T/T | T/T | C/C | 1 | 2349120 | 2 |
| solcap_snp_sl_59890 Δs | A/A | G/G | A/A | 1 | 4597950 | 1 |
| solcap_snp_sl_19066 | C/C | T/T | C/C | 1 | 38118500 | 1 |
| solcap_snp_sl_14042 | T/T | C/C | T/T | 1 | 38274900 | 1 |
| *solcap_snp_sl_18619* * | *G/G* | *T/T* | *G/G* | *1* | *68232900* | *1* |
| *solcap_snp_sl_12348* * | *C/C* | *T/T* | *C/C* | *1* | *72528600* | *1* |
| EP_0180_LC7488 | A/A | C/C | A/A | 1 | 74360500 | 1 |
| EE_2741_LC7681 | C/C | T/T | C/C | 1 | 75365500 | 1 |
| EP_0350_LC6805 | A/A | G/G | A/A | 1 | 76649200 | 1 |
| solcap_snp_sl_15339 Δe | C/C | T/T | C/C | 1 | 77112400 | 1 |
| EE_4184_LC7793 | A/A | A/A | A/G | 1 | 77540500 | 2 |
| SL10357_122_LC6821 | A/A | G/G | A/A | 1 | 77950400 | 1 |
| EE_2138_LC7257 | C/C | G/G | C/C | 1 | 78104200 | 1 |
| IL3_1952_LC7796 | G/G | A/A | G/G | 1 | 78158000 | 1 |
| SL10693_51_LC7809 | C/C | T/T | C/C | 1 | 78236200 | 1 |
| EE_3245_LC6799 | T/T | A/A | T/T | 1 | 78602500 | 1 |
| SL10489_373_LC7781 | G/G | A/A | G/G | 1 | 79286800 | 1 |
| SL10018_198 | A/A | G/G | A/A | 1 | 80408100 | 1 |
| SL10259_474_LC7727 | T/T | T/T | C/C | 1 | 81000900 | 2 |
| solcap_snp_sl_40154 Δs | NA | T/T | NA | 1 | 83517400 | 1 |
| *EP_1592_LC7762 Δe* * | *C/C* | *T/T* | *C/C* | *1* | *83766400* | *1* |
| EP_1027_LC7889 | NA | NA | T/T | 1 | 84256600 | 2 |
| EE_4621_LC7272 | G/G | G/G | A/A | 1 | 86580700 | 2 |
| solcap_snp_sl_14323 | T/T | T/T | C/C | 1 | 86675700 | 2 |
| EE_2225_LC7481 | C/C | C/C | T/T | 1 | 89810700 | 2 |
| solcap_snp_sl_15058 | A/A | A/A | G/G | 1 | | 2 |
| SL20284_556_LC7915 | A/A | A/A | G/G | 2 | 7194740 | 2 |
| solcap_snp_sl_12647 | T/T | T/T | C/C | 2 | 21285100 | 2 |
| EE_1649_LC6737 | G/G | G/G | A/A | 2 | 29006800 | 2 |
| solcap_snp_sl_26072 | C/C | C/C | T/T | 2 | 29095800 | 2 |
| solcap_snp_sl_12372 | T/T | T/T | G/G | 2 | 29750900 | 2 |
| SL10173_770_LC6727 | C/C | C/C | T/T | 2 | 29820500 | 2 |
| solcap_snp_sl_15698 | A/A | A/A | G/G | 2 | 31368100 | 2 |
| EP_1969_LC7960 | A/A | A/A | C/C | 2 | 33261500 | 2 |
| solcap_snp_sl_10557 | C/C | C/C | A/A | 2 | 34683500 | 2 |
| SL10153_153_LC7506 | A/A | A/A | C/C | 2 | 36959600 | 2 |
| SL10360_663 | G/G | G/G | C/C | 2 | 37860200 | 2 |
| SL10735_869_LC7741 | A/A | A/A | NA | 2 | 40095800 | 2 |
| IL2_5828_LC5919 | A/A | A/A | G/G | 2 | 43801800 | 2 |
| solcap_snp_sl_12841 | T/T | T/T | C/C | 2 | 43801800 | 2 |
| SL10040_1076_LC7739 | T/T | T/T | G/G | 2 | 47239000 | 2 |
| CL017436-0294 | C/C | T/T | C/C | 2 | 48687200 | 1 |
| EE_3579_LC7227 | C/C | C/C | T/T | 2 | | 2 |
| solcap_snp_sl_19040 | NA | NA | C/C | 2 | | 2 |
| EE_4397_LC7630 | T/T | T/T | C/C | 3 | 77115 | 2 |
| solcap_snp_sl_9690 | G/G | G/G | A/A | 3 | 2073090 | 2 |
| solcap_snp_sl_14355 | C/C | C/C | T/T | 3 | 7085130 | 2 |
| IL2_3177_LC6317 | T/T | T/T | A/A | 3 | 7669140 | 2 |
| solcap_snp_sl_12718 | T/T | T/T | C/C | 3 | 8904650 | 2 |
| solcap_snp_sl_12722 | G/G | G/G | A/A | 3 | 8943250 | 2 |
| solcap_snp_sl_4937 | T/T | A/A | T/T | 3 | 12866900 | 1 |
| solcap_snp_sl_4932 | A/A | G/G | A/A | 3 | 15380400 | 1 |

TABLE 7-continued

| SNP | TUT115 | LYCO1 | GALA1 | CHROMOSOME | POSITION | Donor/recurrent |
|---|---|---|---|---|---|---|
| EP_0398_LC7890 | G/G | A/A | G/G | 3 | 38800900 | 1 |
| EE_2302 | G/G | T/T | G/G | 3 | 43641500 | 1 |
| solcap_snp_sl_1779 | G/G | T/T | G/G | 3 | 43641500 | 1 |
| EE_2301_LC7799 | C/C | T/T | C/C | 3 | 43641700 | 1 |
| EE_3215_LC7337 | A/A | G/G | A/A | 3 | 45613700 | 1 |
| EE_2132_LC7726 | G/G | A/A | G/G | 3 | 46645300 | 1 |
| EE_4940_LC7305 | G/G | T/T | G/G | 3 | 57629400 | 1 |
| SL10019_376_LC7274 | G/G | A/A | G/G | 3 | 58095800 | 1 |
| IL2_3047_LC7278 | G/G | A/A | G/G | 3 | 58127400 | 1 |
| IL2_3855_LC6626 | C/C | A/A | C/C | 3 | 58199700 | 1 |
| EE_3777_LC7270 | G/G | A/A | G/G | 3 | 58210300 | 1 |
| EE_0718_LC7273 | G/G | A/A | G/G | 3 | 58226900 | 1 |
| SL10385_861_LC7255 | C/C | T/T | C/C | 3 | 58365800 | 1 |
| SL20269_959 | C/C | T/T | C/C | 3 | 58405600 | 1 |
| EE_3736_LC7608 | T/T | C/C | T/T | 3 | 58640000 | 1 |
| EE_2254 | T/T | C/C | T/T | 3 | 58746500 | 1 |
| SGN-U565536_snp46769 | P/P | G/G | P/P | 3 | 59935400 | 1 |
| solcap_snp_sl_15173 | T/T | T/T | A/A | 3 | 60806800 | 2 |
| EE_0928_LC7606 | T/T | T/T | C/C | 3 | 60856300 | 2 |
| EE_0775_LC7309 | G/G | G/G | A/A | 3 | 60862400 | 2 |
| IL3_0122 | T/T | T/T | C/C | 3 | 60934800 | 2 |
| EE_5812 | T/T | T/T | C/C | 3 | 61275100 | 2 |
| SL10976_673_LC7290 | G/G | G/G | A/A | 3 | 62094000 | 2 |
| SL10772_850_LC6617 | G/G | G/G | A/A | 3 | 62815100 | 2 |
| EE_2571_LC8007 | T/T | T/T | C/C | 3 | 63616800 | 2 |
| EE_3501_LC8061 | A/A | A/A | C/C | 3 | 63766900 | 2 |
| EE_2924_LC7831 | G/G | G/G | C/C | 3 | 64397100 | 2 |
| EP_1717_LC8068 | A/A | A/A | G/G | 3 | 64800700 | 2 |
| solcap_snp_sl_55187 | T/T | T/T | C/C | 3 | | 2 |
| CL016669-0383 | C/C | T/T | C/C | 3 | | 1 |
| SL10428_501 | C/C | C/C | T/T | 4 | 2146360 | 2 |
| EE_3260 | NA | NA | C/C | 4 | 9492130 | 2 |
| CL017721-0135 | A/A | A/A | G/G | 4 | 9603600 | 2 |
| EE_4973_LC7241 | C/C | C/C | A/A | 4 | 51709700 | 2 |
| EE_4974_LC7242 | G/G | G/G | A/A | 4 | 51709900 | 2 |
| EE_2179 | G/G | G/G | P/P | 4 | 54197200 | 2 |
| solcap_snp_sl_58921 | G/G | G/G | T/T | 4 | 54409600 | 2 |
| EE_1504 | T/T | T/T | C/C | 4 | 54754300 | 2 |
| EE_1675_LC7556 | A/A | A/A | G/G | 4 | 54846200 | 2 |
| solcap_snp_sl_13133 | A/A | A/A | G/G | 4 | 55086600 | 2 |
| EE_0519_LC7259 | G/G | G/G | A/A | 4 | 55717100 | 2 |
| SL10207_600_LC7235 | C/C | C/C | T/T | 4 | 56139200 | 2 |
| SL10101_673_LC6864 | G/G | G/G | A/A | 4 | 57223700 | 2 |
| EP_0368 | A/A | A/A | G/G | 4 | 57402600 | 2 |
| solcap_snp_sl_11515 | A/A | A/A | G/G | 4 | 57896200 | 2 |
| EE_4324_LC7699 | C/C | C/C | A/A | 4 | 58075600 | 2 |
| EE_4325_LC7718 | G/G | G/G | A/A | 4 | 58075700 | 2 |
| EE_6012_LC7239 | NA | C/C | NA | 4 | 58790800 | 1 |
| SGN-U594049_snp94598 | A/A | G/G | A/A | 4 | 60551900 | 1 |
| IL2_0224_LC7658 | A/A | A/A | G/G | 4 | 62610300 | 2 |
| SL20205_697_LC7245 | G/G | G/G | T/T | 4 | 63672200 | 2 |
| solcap_snp_sl_2011 | A/A | A/A | T/T | 4 | | 2 |
| EE_1982 | A/A | G/G | A/A | 4 | | 1 |
| ***EE_0301 Δe Δs *** | *T/T* | *G/G* | *T/T* | 5 | 3636270 | *1* |
| EE_3810_LC7374 | G/G | G/G | A/A | 5 | 4146540 | 2 |
| EE_4099_LC6860 | C/C | C/C | T/T | 5 | 5887820 | 2 |
| IL2_1979_LC8095 | T/T | T/T | C/C | 5 | 5971710 | 2 |
| EE_2637_LC7698 | A/A | A/A | G/G | 5 | 6160880 | 2 |
| EE_0853_LC6863 | A/A | A/A | T/T | 5 | 6226660 | 2 |
| IL2_4587_LC7087 | G/G | G/G | NA | 5 | 6388250 | 2 |
| EE_0954_LC7212 | C/C | C/C | T/T | 5 | 6457710 | 2 |
| EE_4155_LC6841 | C/C | C/C | T/T | 5 | 6979790 | 2 |
| EE_3256 | A/A | A/A | G/G | 5 | 7492620 | 2 |
| solcap_snp_sl_13798 | C/C | C/C | T/T | 5 | 8156640 | 2 |
| SL10639_108 | G/G | G/G | A/A | 5 | 8215150 | 2 |
| IL3_2338 | T/T | T/T | C/C | 5 | 8967100 | 2 |
| EE_4380 | G/G | G/G | A/A | 5 | 10095100 | 2 |
| IL2_4686_LC5993 | G/G | G/G | T/T | 5 | 10702300 | 2 |
| SL10469_816_LC7368 | T/T | T/T | C/C | 5 | 13142000 | 2 |
| SL10469_202_LC7365 | A/A | A/A | C/C | 5 | 13142700 | 2 |
| EP_0159 | C/C | C/C | T/T | 5 | 16804800 | 2 |
| SL10526_459_LC7321 | A/A | A/A | T/T | 5 | 18738900 | 2 |
| SL10526_144_LC7578 | T/T | T/T | A/A | 5 | 18738900 | 2 |
| IL3_1559_LC7546 | C/C | C/C | A/A | 5 | 19274800 | 2 |
| SL10100_95_LC7314 | T/T | T/T | C/C | 5 | 20574100 | 2 |
| SL10100_757 | G/G | G/G | A/A | 5 | 20574700 | 2 |
| EE_1486_LC7518 | G/G | G/G | A/A | 5 | 23877100 | 2 |

TABLE 7-continued

| SNP | TUT115 | LYCO1 | GALA1 | CHROMOSOME | POSITION | Donor/recurrent |
|---|---|---|---|---|---|---|
| IL1__6687_LC7317 | T/T | T/T | C/C | 5 | 23878300 | 2 |
| CL015854-0378 | T/T | T/T | C/C | 5 | 25878300 | 2 |
| IL2__4983 | T/T | T/T | C/C | 5 | 25878300 | 2 |
| KGe1103_LC7548 | G/G | G/G | T/T | 5 | 39648500 | 2 |
| EE__2817 | A/A | A/A | G/G | 5 | 43177000 | 2 |
| KGe2770_LC7361 | T/T | T/T | C/C | 5 | 45414700 | 2 |
| KGe1882 | G/G | G/G | A/A | 5 | 49402500 | 2 |
| SL10373__526 | T/T | T/T | C/C | 5 | 50849700 | 2 |
| Le001857__68 | C/C | C/C | T/T | 5 | 59037000 | 2 |
| KGe1995 | T/T | T/T | C/C | 5 | 59037100 | 2 |
| SL10724__1217_LC7835 | C/C | C/C | T/T | 5 | 59655900 | 2 |
| solcap_snp_sl__12181 | T/T | T/T | C/C | 5 | 60197900 | 2 |
| Le006551__63 | G/G | G/G | C/C | 5 | 62103800 | 2 |
| EE__5750 | C/C | C/C | T/T | 5 | 62495900 | 2 |
| *EE_4363_LC7656 Δs \** | *G/G* | *T/T* | *G/G* | 6 | 166755 | *1* |
| IL3__2569_LC7566 | G/G | T/T | G/G | 6 | 1649290 | 1 |
| EE__1008_LC7515 | T/T | C/C | T/T | 6 | 1674080 | 1 |
| solcap_snp_sl__65595 | A/A | C/C | A/A | 6 | 3299310 | 1 |
| solcap_snp_sl__32320 | C/C | T/T | C/C | 6 | 5388530 | 1 |
| solcap_snp_sl__30498 | G/G | T/T | G/G | 6 | 6794900 | 1 |
| solcap_snp_sl__30511 | G/G | A/A | G/G | 6 | 8159800 | 1 |
| solcap_snp_sl__31156 | G/G | T/T | G/G | 6 | 12040400 | 1 |
| SL10187__425 | A/A | G/G | A/A | 6 | 12751900 | 1 |
| Le004790__246 | T/T | C/C | T/T | 6 | 20347900 | 1 |
| EP__0572_LC7445 | T/T | C/C | T/T | 6 | 21806900 | 1 |
| EE__2362 | C/C | T/T | C/C | 6 | 29418200 | 1 |
| SL10768__133 | C/C | T/T | C/C | 6 | 33808800 | 1 |
| EE__2996 | C/C | T/T | C/C | 6 | 34459100 | 1 |
| solcap_snp_sl__14452 | A/A | G/G | A/A | 6 | 35101900 | 1 |
| SL10539__786_LC7260 Δe | T/T | G/G | T/T | 6 | 35194800 | 1 |
| solcap_snp_sl__12646 | T/T | C/C | T/T | 6 | 35677700 | 2 |
| solcap_snp_sl__12638 | G/G | T/T | G/G | 6 | 36179000 | 1 |
| solcap_snp_sl__12746 | C/C | T/T | C/C | 6 | 36927900 | 1 |
| EE__0212_LC7755 | G/G | A/A | G/G | 6 | 41542800 | 1 |
| EE__5803_LC7716 | T/T | T/T | C/C | 6 | 44134700 | 2 |
| EP__1913_LC7870 | A/A | A/A | G/G | 6 | 44542800 | 2 |
| SL20164__562_LC7140 | C/C | C/C | T/T | 6 | 44857700 | 2 |
| EE__0497_LC7340 | T/T | T/T | C/C | 6 |  | 2 |
| solcap_snp_sl__11233 | C/C | T/T | C/C | 7 | 670304 | 1 |
| EE__3711_LC10116 | T/T | C/C | T/T | 7 | 994270 | 1 |
| solcap_snp_sl__11205 | C/C | A/A | C/C | 7 | 1375140 | 1 |
| EE__1788_LC7194 | T/T | C/C | T/T | 7 | 2240720 | 1 |
| EE__2398_LC7918 | G/G | T/T | G/G | 7 | 2893460 | 1 |
| IL2__1573_LC6628 | T/T | C/C | T/T | 7 | 3147390 | 1 |
| EE__4619_LC7594 | G/G | A/A | G/G | 7 | 3835460 | 1 |
| solcap_snp_sl__26437 | T/T | C/C | T/T | 7 | 54697000 | 1 |
| EE__0993_LC7772 | C/C | T/T | C/C | 7 | 55130300 | 1 |
| solcap_snp_sl__14172 | C/C | A/A | C/C | 7 | 58092200 | 1 |
| CL016778-0295 | T/T | A/A | T/T | 7 | 59114500 | 1 |
| 3081__1__53 | C/C | A/A | C/C | 7 | 60325200 | 1 |
| SL10719__49_LC7694 | A/A | A/A | C/C | 7 | 61079400 | 2 |
| SL10041__719_LC7675 | A/A | A/A | G/G | 7 | 61094800 | 2 |
| EP__0109_LC7882 | A/A | A/A | G/G | 7 | 61194700 | 2 |
| EE__4765_LC7703 | A/A | A/A | G/G | 7 | 62265100 | 2 |
| EE__2310_LC7448 | A/A | A/A | G/G | 7 | 62465700 | 2 |
| EE__5773_LC7638 | T/T | T/T | NA | 7 | 62473000 | 2 |
| EE__5366 | G/G | G/G | A/A | 7 |  | 2 |
| EE__6087_LC7761 | T/T | T/T | C/C | 8 | 602770 | 2 |
| solcap_snp_sl__4431 | G/G | C/C | G/G | 8 | 50440200 | 1 |
| solcap_snp_sl__21394 | G/G | A/A | G/G | 8 | 55659500 | 1 |
| EE__1326_LC6848 | T/T | C/C | T/T | 8 | 55997400 | 1 |
| EP__0889_LC6813 | T/T | C/C | T/T | 8 | 56053100 | 1 |
| solcap_snp_sl__21401 | C/C | G/G | C/C | 8 | 56202000 | 1 |
| EE__3574_LC7825 | T/T | T/T | C/C | 8 | 58036300 | 2 |
| IL3__0456 | T/T | T/T | G/G | 8 | 59248400 | 2 |
| solcap_snp_sl__15432 | A/A | T/T | A/A | 8 | 60016900 | 1 |
| EE__1024 | A/A | G/G | A/A | 8 | 60035000 | 1 |
| solcap_snp_sl__10181 | T/T | A/A | T/T | 8 | 61303500 | 1 |
| solcap_snp_sl__29404 | G/G | T/T | G/G | 8 |  | 1 |
| CL015323-0211 | A/A | C/C | A/A | 8 |  | 1 |
| EP__0489_LC7684 Δs | C/C | T/T | C/C | 9 | 3897960 | 1 |
| SL10004__409_LC7341 | A/A | G/G | A/A | 9 | 4063240 | 1 |
| IL2__5178 | NA | T/T | NA | 9 | 7854930 | 1 |
| EE__1577_LC7366 | G/G | A/A | G/G | 9 | 11226500 | 1 |
| EE__1758_LC7427 | NA | A/A | NA | 9 | 18614700 | 1 |
| *CL016475-0340 \** | *A/A* | *G/G* | *A/A* | 9 | 22094800 | *1* |
| *EP__0502 \** | *C/C* | *A/A* | *C/C* | 9 | 41847000 | *1* |

TABLE 7-continued

| SNP | TUT115 | LYCO1 | GALA1 | CHROMOSOME | POSITION | Donor/recurrent |
|---|---|---|---|---|---|---|
| *EE_4969_LC7529* * | *A/A* | *G/G* | *A/A* | 9 | 49173600 | *1* |
| *EE_2332* * | *T/T* | *C/C* | *T/T* | 9 | 54692600 | *1* |
| IL2_1262 | T/T | C/C | T/T | 9 | 62444900 | 1 |
| EE_1817_LC6849 | A/A | G/G | A/A | 9 | 62491400 | 1 |
| EE_3482_LC7808 | C/C | A/A | C/C | 9 | 63350800 | 1 |
| EE_5152_LC7199 | A/A | G/G | A/A | 9 | 63473800 | 1 |
| *EE_1452 Δe* | *T/T* | *C/C* | *T/T* | 9 | 63642500 | *1* |
| EE_1806_LC7215 | C/C | C/C | T/T | 10 | 274856 | 2 |
| CL015614-0412 | G/G | C/C | G/G | 10 | 468922 | 1 |
| solcap_snp_sl_13200 | C/C | G/G | C/C | 10 | 1058430 | 1 |
| EE_0324 | T/T | T/T | C/C | 10 | 2746430 | 2 |
| SGN-U603133_snp167 | T/T | T/T | C/C | 10 | 3092680 | 2 |
| EE_2689 | A/A | A/A | NA | 10 | 7364210 | 2 |
| CL017204-0355 | A/A | A/A | NA | 10 | 7364210 | 2 |
| EP_1264_LC7935 | NA | NA | A/A | 10 | 28869300 | 2 |
| EE_6135 | A/A | A/A | G/G | 10 | 49992900 | 2 |
| solcap_snp_sl_5191 | G/G | G/G | C/C | 10 | 51147000 | 2 |
| solcap_snp_sl_5186 | T/T | T/T | C/C | 10 | 52254300 | 2 |
| EE_4309 | A/A | A/A | C/C | 10 | 52670500 | 2 |
| solcap_snp_sl_16501 | C/C | C/C | G/G | 10 | 57997200 | 2 |
| SL10843_69_LC7861 | T/T | T/T | C/C | 10 | 59085800 | 2 |
| solcap_snp_sl_13113 | G/G | G/G | T/T | 10 | 59255100 | 2 |
| EP_0902_LC6716 | G/G | G/G | A/A | 10 | 60698100 | 2 |
| IL3_2005_LC7733 | T/T | T/T | NA | 10 | 61823700 | 2 |
| EE_3505_LC7711 | A/A | A/A | G/G | 10 | 61957300 | 2 |
| IL2_1143_LC7218 | G/G | G/G | A/A | 10 | 62066300 | 2 |
| EE_0009_LC7600 | T/T | T/T | C/C | 10 | 62724400 | 2 |
| SL10786_261_LC7236 | C/C | C/C | T/T | 10 | 62802900 | 2 |
| SL20016_1557_LC7848 | T/T | T/T | C/C | 10 | 64632700 | 2 |
| EE_3347_LC7683 | T/T | T/T | C/C | 10 | 64633300 | 2 |
| solcap_snp_sl_15641 | C/C | G/G | C/C | 11 | 436090 | 1 |
| EE_0570 | A/A | G/G | A/A | 11 | 502389 | 1 |
| solcap_snp_sl_10611 | T/T | T/T | A/A | 11 | 1988860 | 2 |
| EP_1258_LC7710 | T/T | T/T | C/C | 11 | 3626710 | 2 |
| solcap_snp_sl_15269 | G/G | G/G | A/A | 11 | 5389480 | 2 |
| SL10640_256_LC7686 | A/A | A/A | C/C | 11 | 6410110 | 2 |
| SL10640_602_LC7666 | T/T | T/T | C/C | 11 | 6410460 | 2 |
| solcap_snp_sl_14367 | A/A | A/A | C/C | 11 | 7715560 | 2 |
| solcap_snp_sl_13506 | C/C | C/C | T/T | 11 | 8640020 | 2 |
| EE_4860_LC7564 | G/G | G/G | C/C | 11 | 8753140 | 2 |
| EE_1605_LC7308 | A/A | A/A | G/G | 11 | 9837710 | 2 |
| EE_4181_LC7643 | G/G | G/G | A/A | 11 | 10019300 | 2 |
| EE_2849_LC7237 | A/A | A/A | NA | 11 | 15654300 | 2 |
| CL016179-0556 | A/A | A/A | G/G | 11 | 35287700 | 2 |
| solcap_snp_sl_13126 | C/C | C/C | T/T | 11 | 35863500 | 2 |
| solcap_snp_sl_13123 | T/T | T/T | C/C | 11 | 36376700 | 2 |
| solcap_snp_sl_10890 | C/C | C/C | T/T | 11 | 45230400 | 2 |
| solcap_snp_sl_10899 | C/C | C/C | T/T | 11 | 45816700 | 2 |
| solcap_snp_sl_10900 | C/C | C/C | T/T | 11 | 45816800 | 2 |
| solcap_snp_sl_10969 | G/G | G/G | A/A | 11 | 46395700 | 2 |
| EE_4526 | A/A | A/A | C/C | 11 | 47595400 | 2 |
| EP_1594_LC6817 | C/C | C/C | A/A | 11 | 49928100 | 2 |
| IL3_1995_LC6827 | G/G | G/G | A/A | 11 | 50098600 | 2 |
| EE_3018_LC7246 | C/C | C/C | T/T | 11 | 51502700 | 2 |
| EE_4777_LC7555 | T/T | T/T | C/C | 11 | 52142200 | 2 |
| EE_1598_LC6842 | G/G | G/G | A/A | 11 | 52225900 | 2 |
| EE_1639_LC8071 | T/T | T/T | C/C | 11 | 52645000 | 2 |
| SL10027_680_LC7770 | A/A | A/A | T/T | 11 | 53186500 | 2 |
| solcap_snp_sl_15247 | A/A | A/A | G/G | 11 | | 2 |
| EE_5199_LC7352 | T/T | T/T | C/C | 11 | | 2 |
| *SL10204_1269 Δs* * | *C/C* | *T/T* | *C/C* | 12 | 124598 | *1* |
| *SGN-U573565_snp665* * | *A/A* | *T/T* | *A/A* | 12 | 155493 | *1* |
| *EE_0924 Δe* * | *T/T* | *C/C* | *T/T* | 12 | 1166000 | *1* |
| solcap_snp_sl_1495 | A/A | A/A | G/G | 12 | 3252080 | 2 |
| SL10795_222 | A/A | A/A | G/G | 12 | 3767860 | 2 |
| solcap_snp_sl_14758 | T/T | T/T | C/C | 12 | 4462020 | 2 |
| IL3_0004 | A/A | A/A | G/G | 12 | 4462020 | 2 |
| solcap_snp_sl_9707 | A/A | A/A | C/C | 12 | 5718730 | 2 |
| solcap_snp_sl_59718 | A/A | A/A | G/G | 12 | 6660010 | 2 |
| solcap_snp_sl_24755 | G/G | G/G | C/C | 12 | 7801440 | 2 |
| EE_3447 | C/C | C/C | T/T | 12 | 8948060 | 2 |
| solcap_snp_sl_40598 | G/G | G/G | A/A | 12 | 8948060 | 2 |
| solcap_snp_sl_1289 | G/G | G/G | A/A | 12 | 9917930 | 2 |
| solcap_snp_sl_1295 | T/T | T/T | C/C | 12 | 12758600 | 2 |
| solcap_snp_sl_40622 | T/T | T/T | G/G | 12 | 12760400 | 2 |
| SL10352_214_LC7623 | T/T | T/T | C/C | 12 | 12871800 | 2 |
| EE_4807_LC7624 | T/T | T/T | C/C | 12 | 14337200 | 2 |

TABLE 7-continued

| SNP | TUT115 | LYCO1 | GALA1 | CHROMOSOME | POSITION | Donor/recurrent |
|---|---|---|---|---|---|---|
| EE_5237 | NA | NA | G/G | 12 | 14640400 | 2 |
| EE_5238_LC7619 | A/A | A/A | G/G | 12 | 14640600 | 2 |
| solcap_snp_sl_53084 | T/T | T/T | C/C | 12 | 17503100 | 2 |
| solcap_snp_sl_53090 | T/T | T/T | C/C | 12 | 19452500 | 2 |
| solcap_snp_sl_17184 | G/G | G/G | A/A | 12 | 23240100 | 2 |
| solcap_snp_sl_42961 | A/A | A/A | T/T | 12 | 24101300 | 2 |
| EE_0461 | T/T | T/T | C/C | 12 | 37136500 | 2 |
| solcap_snp_sl_52407 | T/T | T/T | C/C | 12 | 37672700 | 2 |
| solcap_snp_sl_59087 | T/T | T/T | G/G | 12 | 39221700 | 2 |
| EP_0926_LC7289 | G/G | G/G | A/A | 12 | 40771200 | 2 |
| solcap_snp_sl_59093 | T/T | T/T | C/C | 12 | 40776000 | 2 |
| solcap_snp_sl_52539 | G/G | G/G | A/A | 12 | 42568300 | 2 |
| EP_0768_LC7607 | A/A | A/A | G/G | 12 | 43619100 | 2 |
| EE_0865_LC7616 | T/T | T/T | C/C | 12 | 43643700 | 2 |
| 3132_3_136 | C/C | C/C | T/T | 12 | 43645100 | 2 |
| EE_3443_LC7302 | G/G | G/G | A/A | 12 | 43799100 | 2 |
| EE_5488 | A/A | A/A | C/C | 12 | 44347200 | 2 |
| EE_4018_LC7618 | A/A | A/A | G/G | 12 | 44634400 | 2 |
| solcap_snp_sl_12389 | T/T | T/T | C/C | 12 | 44709600 | 2 |
| EP_1486_LC7832 | A/A | A/A | G/G | 12 | 63255200 | 2 |
| SL10823_84_LC7816 | A/A | A/A | G/G | 12 | 63538200 | 2 |
| SL10329_708_LC6736 | C/C | C/C | A/A | 12 | 63612300 | 2 |
| EE_3321_LC7974 | A/A | A/A | G/G | 12 | 64623500 | 2 |
| SL10284_439 | A/A | A/A | G/G | 12 | 65136500 | 2 |
| EE_5042_LC6684 | C/C | C/C | T/T | 12 | 65148800 | 2 |

Conclusion

Twelve markers were significantly associated with the PLA measure of resistance to South America tomato pinworm, together explaining 55% of the observed phenotypic variance. Nine of these markers are also significantly associated with other measures of resistance, namely LLT and OPD, which reinforce the confidence of these markers. The significant correlation to different measures of the traits suggests these markers are linked to a general resistance mechanism.

Marker Validation

Markers are validated by crossing line TUT115, which displayed the highest resistance relative to all tested RILs, with a susceptible line. The resulting F1 is selfed, and a large population of F2 seeds is collected. Plants are grown and genotyped. A selection of the F2 progeny is selfed to F3. The F3 families are phenotyped as described in example 1. The linkage of each marker to the resistance phenotype is assessed.

Breeding Plan

From the above described F2 plants, a set is selected. Each F2 plant carry a subset of the validated markers, where all selected F2 plants together cover all validated markers. Each F2 plant is backcrossed to a breeding line in a marker assisted backcross scheme. Plants having the relevant markers as well as the highest percentage of breeding line markers are selected to a second round of backcrossing. This process is repeated to a third backcross round resulting in a set of lines with a high percentage of breeding line background, each having a homozygous subset of the markers linked to the required resistance. Next the lines are crossed in turn in order to accumulate ("pyramid") all required markers into one line or commercial variety.

Discussion

The resistance to South American Pinworm is a complex trait, probably defined by several genes {Maluf 1997, 2010a}. The inventors describe here the identification of a resistant source, and resistant recombinant inbred lines devised from this source. In addition, they identified a group of markers significantly correlated with the resistance, identifying the resistant line.

Since this trait is highly affected by environment {Resende 2002}, not all the observed variance is however explained by the genetic markers as shown by the calculated heritability of 0.6.

Example 3

Determine Resistance of Identified RIL's of GALA1 Against Additional Organisms

Spider Mites (*Tetranychus urticae*)

Materials and Methods

Experimental Design

In an experimental choice setting, 19 genotypes were tested for their suitability to rear spider mites on. Test plants were grown, as described in section Tomato germplasm rearing (Example 1), until plants reached the stage of having 4 true leaves. A genotype's suitability for spider mite rearing was measured by scoring feeding symptoms in combination with observed mites and webbings constructed by the mite species under testing. The experiment contained two experimental repetitions over time, per experimental repetition there were 3 repeats with each 11 seedlings per genotype (26° C.; 16 hr light:8 hr dark).

Infestation Method:

Test plants were infested three weeks after sowing by placing heavily infested leaves from the spidermite rearing face down on the test plants. The leaves used for infestation were placed close to each other in order to create a surface of leaves above the test plants. After infestation, plants were irrigated using a flooding system. Two days after infestation the leaves that were used for infestation were removed.

Scoring Method:

The spidermite population reached a peak after two to three weeks. Three weeks post infestation feeding damage levels were scored. The susceptible or resistant plants were defined by the amount and the distribution of the population and were indexed by a scale from 0-3 (see below):

0—A clean leaf without mites or tissue-feeding damage. Note: a number of mites centered on one place on the leaf could still be observed.

1—Presence of mites in a defined area that did not cover the entire leaf. In this area feeding symptoms were observed. Leaves continued to develop, but the mite population did not grow.
2—A leaf surface was covered with mites and clear feeding damage symptoms were noticed.
3—A leaf is covered with mites and webs. Leaves showed clear chlorosis or necrosis symtomps.

Figure 4:
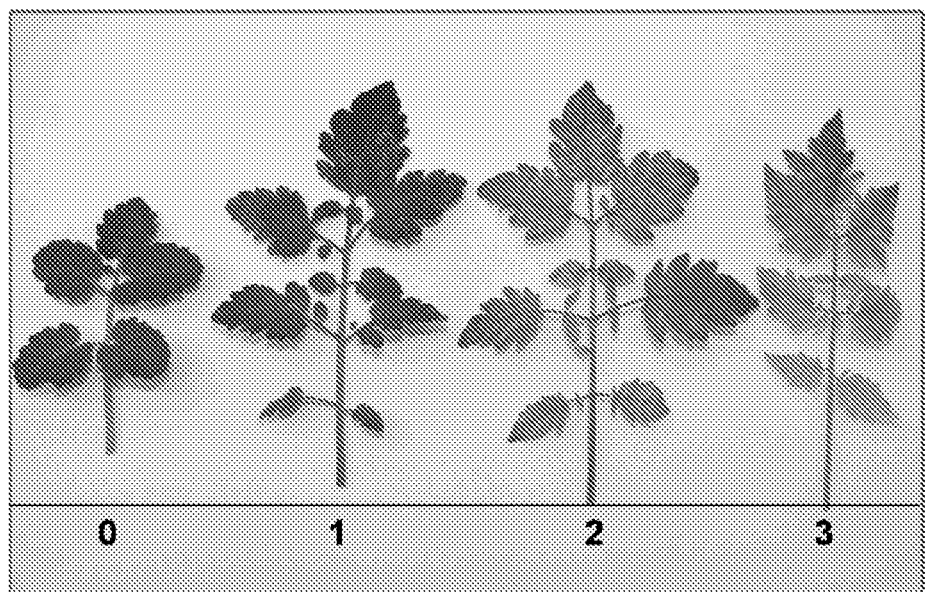
FIG. 4 illustrates the spider mite feeding damage scaling.

Plant symptoms from 0-1 indicate resistant plants. Plants symptoms from 2-3 indicate susceptible plants (see FIG. 4 for illustration).
Results:

Resistance levels for the individual RIL-lines were compared to resistance levels from the recurrent parent, i.e. LYCO1, using an Hsu-Dunnett LSMeans Difference test. The mean score from each tested line was adjusted by entering observation notes as an effect into the linear model. Obtained data indicated that almost all tested RIL lines were significantly more resistant against spider mites when compared to the recurrent parent (see FIG. 5).
Conclusion:

Tested RIL lines were mostly resistant, but these lines were less resistant compared to donor GALA1. Therefore it is concluded that the donor and also most of the RIL lines contain resistance traits that hamper population build up for the tested spidermite species, which is determined by scoring the population distribution per genotype using feeding symptoms and mite and webbing density as parameters.
White Fly (*Bemicia tabaci*)
Materials and Methods
Experimental Design In a choice assay RIL leads were tested for resistance against the Hemiptera white fly. As a measure of resistance the success of building up a white fly population on a plant was scored by counting numbers of newly developed white fly nymphs. Tested RIL-lines TUT103, TUT112, TUT115, and the donor GALA1, the recurrent parent LYCO1 and pinworm rear line LYCO2, were grown as described in section Tomato germplasm rearing (Example 1). Experimental plants were randomly divided over three experimental cages (0.9 m width*8.0 m length*0.6 m height) in a greenhouse (temperature: +/−30° C. day and +/−20° C. night). Experimental cages hosted at least 6 plants per tested germplasm. Three consecutive fully developed leaves were marked starting at the top of a plant.
Infestation Method:

For infestation an on cotton reared white fly colony was used. Infestation was conducted by introducing approximately one hundred 5-10 days old adult white flies per test plant.

Introduced adults were allowed to oviposit for seven days after which they were killed with insecticide Talstar (pyrethroid Bifenthrin).
Scoring Method:

Fourteen days after infestation nymphs were counted from the bottom side of the prior marked leaves. For this end, five randomly 2 cm$^2$ areas per leave were screened for nymphs using a magnifying glass (6×).
Results:

Number of nymphs per leaf were measured. Mean number of nymphs per genotype were adjusted by using the table and the leaf position as an effect in a linear model. Obtained data was compared using a Tukey Kramer test. All RIL lines were significantly more resistant

TABLE 8

Tomato resistance against white fly.
Mean number of white fly nymphs were analyzed using a Tukey Kramer HSD test: genotypes with the same sign. grouping letter do not differ significantly.

| Germplasm | Mean number of nymphs | SE | Least Sq mean | Sign. grouping | | |
|---|---|---|---|---|---|---|
| GALA1 | 12.23 | 1.87 | 11.76 | | C | |
| TUT112 | 4.59 | 1.46 | 4.79 | D | | |
| TUT115 | 10.15 | 1.52 | 9.95 | D | C | |
| TUT103 | 19.45 | 1.36 | 19.27 | | | B |
| LYCO1 | 26.05 | 1.52 | 25.85 | | | A |

Conclusion

All tested genotypes were more resistant against white flies compared to recurrent parent LYCO1. Moreover, this bioassay indicate that tested RIL line TUT112 is more resistant against white fly population build (i.e. nymph presence) compared to donor GALA1.
Western Flower Thrips (*Franklienella occidentalis*)
Materials and Methods Resistance traits from identified promising RIL leads were tested against the Thysanoptera insect *F. occidentalis*. Promising resistant tomato RIL-lines, the donor and the recurrent parent were sown and reared in nursery trays (54 holes of 2″/tray) filled with rockwool plugs. Seedlings having 1-2 true leaves were transplanted on rockwool (10*10*6.5 cm). Sixteen plants per germplasm were transferred to an insect free greenhouse for further development, and divided over two cages. When plants had 5-8 true leaves, they were infested with 20 thrips per plant. Feeding damage was scored by scoring the number of leaflets infested for consecutive true leaves A, B, & C, started counting from the cotyledons.
Results Resistance levels for the individual RIL-lines were compared to resistance levels from the recurrent parent, i.e. LYCO1, using an Hsu-Dunnett LSMeans Difference test (see FIG. 6). The mean score from each tested line was adjusted by entering observation notes as an effect into the linear model.
Conclusion:

RIL-lines TUT101 and TUT115 were significantly more resistant against thrips damage compared to recurrent parent LYCO1. These two RIL-lines showed GALA1 levels of resistance against thrips.
Tomato Russet Mite (*Aculopus lycopersici*)
Materials and Methods
Experimental Design In a non-choice experimental setting, 5 genotypes were tested for its suitability to build up a russet mite population. Test plants were grown, as described in section Tomato germplasm rearing (Example 1), until plants reached the stage of having 6-8 true leaves. A genotype's suitability for population build up was measured by scoring feeding symptoms in combination with observed severeness of the russet mite population.
Infestation Method:

Test plants were infested six weeks after sowing by placing heavily infested leaves from a tomato russet mite rearing face down on the test plants. After infestation, plants were regularly irrigated using 20:20:20 NPK. Two days post infestation used leaves for infestation were removed (26° C.; 16 hr light:8 hr dark regime).
Scoring Method:

The tomato russet mite population was scored 2 weeks after infestation by determining the severeness of the present russet mite population and the observed feeding symptoms.

Results:

TABLE 9

Resistance against the tomato russet mite.

| genotype | Russet mite population | Feeding symptoms |
|---|---|---|
| LYCO2 | Abundant | severe necrosis + chlorosis |
| TUT103 | Abundant | severe necrosis + chlorosis |
| TUT110 | Abundant | severe necrosis + chlorosis |
| TUT115 | Poor | some necrosis |
| GALA1 | Poor | some necrosis |

Conclusion:

Obtained qualitative data suggested that TUT115 contain the resistance characteristics from donor GALA1 that could cause non-preference.

Example 4

Flanking Sequences of the SNPs of the Invention

The flanking sequences of the 12 SNPs of the invention and of the 12 alternative SNPs of the invention are hereby given in table 10.

TABLE 10

| SNP | 5' flanking sequence | 3' flanking sequence |
|---|---|---|
| solcap_snp_sl_18619 | CAAAATTTGGGAGAGCTGAAGCAGAGTTTCCCACTCAAGGTAAATGTATA (SEQ ID N. 1) | AGCTAGTCAAAAGTATGCCAGTTGTGTCCTGTTGCTTGTGTATATAGTTC (SEQ ID N. 2) |
| solcap_snp_sl_12348 | AGTCTCTAACAATCAAGTTGGTGGGGATATAGGCTCAGACATTGAGCTGG (SEQ ID N. 3) | ACATTCATCTGATTCCGATCAAGAAGTTGATGATTACGATGACCTTCCAC (SEQ ID N. 4) |
| EP_1592_LC7762 | GAGAAAAAGACCATTAGACAAAGAAAAGGTGTTTTGATAGCTACGGAGAAAAAGAGAAAG (SEQ ID N. 5) | ATAGAGAAAAAAAGCAAAACAGGGAGATGAAAGGGGTCTCTAATGGGAGATCCATTCCCT (SEQ ID N. 6) |
| EE_0301 | TAAACTAAAGTCTCCTTTTATTTTTCATCAATAACCTTATAACTAACTTAACTAAAAACA (SEQ ID N. 7) | AGGCAATTTTTATCCACACCAAATATAAAACTAAACTTAAATCCCCATTTTCCAAGACAT (SEQ ID N. 8) |
| EE_4363_LC7656 | CTGAAGGTCCAGACCACCTGTACTGCCCTTCTCCACACCTATGTCCAGCATAAGGACACT (SEQ ID N. 9) | CTAAAGCTGAGTCTTTGATGGAAAAAATGTCTGAATGCGGGGTTCTGAAGTACCCTCTTC (SEQ ID N. 10) |
| CL016475-0340 | AATAATCTCCCCTCCTTTAAACTTGGAGTATTTGAATATCACTGTTTCCGATCCACACAAGGAAATACAAGCATCCCCCTCAATTGTTCCTGGCACTAAT (SEQ ID N. 11) | CTTATGTNACCTATTTAATTACCACACAAACCAATTTACCTGATTATGGAGGAACCGATTTCANTGTTCGTAGACGCTTTAAAGACATTGTTACTTTATC (SEQ ID N. 12) |
| EP_0502 | GATGATGAAAAGGTGGATTATTCACAAGTACTTTCTGCATTGCTTCCTTTTGTTGTGGCC (SEQ ID N. 13) | TCACTGCTGTTGCTGCTCTTTCTCACCCTTCAACTTTCACATGGGTTTCTAAAGATTTGT (SEQ ID N. 14) |
| EE_4969_LC7529 | GCCGGGGATAGCTAACACACCAATATTATTAATTTAGAGAATCAATTATGGAGATC (SEQ ID N. 15) | ATGGGAACTCAAATGATGTTCTTCACATAGTTTTGTTCCCTTTTTTTCGCATTTGGTCAT (SEQ ID N. 16) |
| EE_2332 | AAGTTGCAAGAGTTGCTTTTGCCTCGCTTCTCTTGTTGATGCTGATGCTATAGTAACTTC (SEQ ID N. 17) | GAATGGGTTCCTACCATTGACCAAATGCTTCTCATGACCAGCATAGTCCTTACATATATA (SEQ ID N. 18) |
| SL10204_1269 | GTCTAGTATTGTTGTAAGAATGCTGGAAGAGGCATTTGTGATTATAAAAGAAACTTGGCA (SEQ ID N. 19) | GATATAGGTTATAACACAGCATAAATCTATATCTAATTCACTTGAACATTACACAAGAAG (SEQ ID N. 20) |
| SGN-U573565_snp665 | GGCTTCAATATTGACTGTAATGAAGGAGATTTCTGATACATTGTACCCAA (SEQ ID N. 21) | GCCTGTCGTGATTTTTAATCCTAAATGGGTTTTGATGAAGAGAGTAGTT (SEQ ID N. 22) |
| EE_0924 | TATTACGGAATCTACTGTAACGTTATCAGAAGCTCTGTCTGAACTTCCAGGTGAAAGGAC (SEQ ID N. 23) | GAAGGTGGTTCTATATCCCTAGATGCCTTGTCTTGCGAGAACCATGAAATAAAGAAGATG (SEQ ID N. 24) |
| EE_1452 | GTCGCAAGATGCGTGAGATCATGGTTAACCAGGCACAATCGTGTGATTTGAAAGACTTGG (SEQ ID N. 25) | CCTGAAGTTCATTCCTGAATCAATCGGTAGAGAGATTGAGAAGGCAACTTCAAGCATCTA (SEQ ID N. 26) |
| EE_2996 | ATGGGTTGGTTTTGGAGAACATATCGTATGGGCAGCTTCAGGCGCTTTCAGCTGTGCCTG (SEQ ID N. 27) | AGATAGTCACTCTTTGTTGACTGAGGAAAGAGGCGGGGAAGGTAGTGGGAGTGGTTCATA (SEQ ID N. 28) |
| IL2_5178 | TTACTCTTCGGTGTTTGAGGATCTTGTTGCAGAGGGTTTTTGAGCCCAAATTCAAAAAC (SEQ ID N. 29) | CTTTGCGTTGAAACACCGATGGGTTCTGATGTTTTTGCGTTGAGGGAAATTGGGGTAGCC (SEQ ID N. 30) |

TABLE 10-continued

| SNP | 5' flanking sequence | 3' flanking sequence |
|---|---|---|
| EE_2362 | AGTTCCAATTCACGAAATCGAAGCCTT CCAACTCTCATCCACGCTTGGTGATT GCAAAGG (SEQ ID N. 31) | CTTGGGGACCGGCGATAATGGTGACTT TGAACATTTTACAGCTACACCTAACAAG ATTTT (SEQ ID N. 32) |
| SL10187_425 | TTTTTACTTTTAAATTTTGCTGTTTGTG AAGTAGGGATATGAATAAAATT (SEQ ID N. 33) | TTGGTCCCTTCTTGTACAATAGGAATGT AAGAACTAGCATATGAGGGATC (SEQ ID N. 34) |
| solcap_snp_sl_15339 | AAGAGGGCAAAAAATGGCTGTAGCAC TCTTGGGGAGTATTTCCTTTTCCT (SEQ ID N. 35) | CTCCATGCCTTCTATATCTTCCCCTTCT CTCCAACACCCTTTCAACTTCA (SEQ ID N. 36) |
| solcap_snp_sl_32320 | AACGCCAGCAATGGAAAAGCAACTTG AGATCGCGTCCACAGTTGGTGCAT (SEQ ID N. 37) | GGTTGCTAAATCCAACCAGCCCAATGA AGTAGGTGATTTTGGTGGTAGTT (SEQ ID N. 38) |
| solcap_snp_sl_40154 | GGCGCCTAGAACTGCTTCTTCTTTTCT TGTGACGCGAACTTCTGTCTCTT (SEQ ID N. 39) | TCTCATCCAACCACTCACTGCTGGAATC TGTATTACGATCTTCCTTGCTA (SEQ ID N. 40) |
| solcap_snp_sl_59890 | ATGTTAACTGAAATTGCATACATCCAC GTTAACAGGAAAACATCGTAGTC (SEQ ID N. 41) | CTTCTAGCAAGAACTTTTTACCCTGTAA TTTGAAATCCAACAAACCCAGA (SEQ ID N. 42) |
| EP_0489_LC7684 | AAACCCCAATTTCTCCGGCCGATCAG TTCTCCTCTTTGTTGATCTCATTTTTCG ATTCTC (SEQ ID N. 43) | GATCACTTTACAGATCCGATTTCGAGTC ACTTCCGAATCGGATCCGGGTCAGATG GCGGC (SEQ ID N. 44) |
| EE_3482_LC7808 | CTAGACAGTAGTGACCAAACTCTTGG TGTTCCGCGTAAGTTTTAGAGTATAAT AAACCCA (SEQ ID N. 45) | AGGACTCGAAAAACATTAGCTCAGATG ATGATGACCTTGTGTAAATTTTCGTATT GGTAT (SEQ ID N. 46) |
| SL10539_786_LC7260 | CTCTAGCCCATCCTTTATACACAGAAG GGCGCAGCCACATCGGGAGTTCCTG GACGAACA (SEQ ID N. 47) | AGCATGGAGTCAAGTTTTTGCTGAATCT TCTGTTATTTAAAATTGATAGAGACTTAC CAC (SEQ ID N. 48) |

REFERENCES

De Azevedo et al.; Euphytica 134:347-351 (2003)
Barrett et al. Bioinformatics 21(2): 263-265 (2005)
Bombarely et al.; Nucleic Acids Res. January; 39: D1149-D1155 (2011)
Broman and Sen; A guide to QTL Mapping with R/qtl. Springer (2009)
Ecole et al.; J. Appl. Ent. 125, 193-200 (2001)
Eigenbrode and Trumble; J. Amer. Soc. Hort. Sci 118(4): 525-530 (1993)
Lewontin. Genetics 49 (1): 49-67, (1964)
Maluf et al. Euphytica 93 (2): 189-194; (1997)
Maluf et al. Euphytica 176:113-123; (2010a)
Maluf et al. Crop Science, vol 50, 439-450; (2010b)
Momotaz et al., J. Amer. Soc. Sci. 135(2):134-142 (2010)
Oliveira et al., Scientia Horticulturae 199; 182-187 (2009)
Resende et al. Genet. Mol. Res. 1(2): 106-116; (2002)
Resende et al.; Sci. Agric., v. 63, n. 1; 20-25; (2006)
Schoonhoven et al. Insect-Plant Biology. Chapmann & Hall (1998)
Zar, Biostatistical Analysis. Fifth Edition. Prentice Hall, (2010)
Zadoks et al. (1974). *Weed Research* 14 (6): 415-421

---

The invention claimed is:

1. A *Solanum lycopersicum* plant, which is resistant to an arthropod pest and resistant to ToMV (Tomato Mosaic Virus), comprising in its genome sequences which are introgressed from *Solanum* galapagense and which confer resistance to said arthropod pest,
wherein said introgressed sequences are chosen from the introgressed sequences present in the genome of a plant of the line TUT115 NCIMB accession number 42109 and include
   a) the fragment corresponding to that comprised between and including SNPs solcap snp sl 59890 at position 4597950 of chromosome 1, on the tomato genome version 2.40 and solcap snp sl 15339 at position 77112400 of chromosome 1, on the tomato genome version 2.40, in chromosome 1 of a plant of the line TUT115 NCIMB accession number 42109 and
   b) the fragment corresponding to that comprised between and including SNPs solcap snp sl 40154 at position 83517400 of chromosome 1, on the tomato genome version 2.40 and EP 1592 LC7762 at position 83766400 of chromosome 1, on the tomato genome version 2.40, in chromosome 1 of a plant of the line TUT115 NCIMB accession number 42109, and
   c) the fragment corresponding to that comprised between and including SNPs EE 4363 LC7656 at position 166755 of chromosome 6, on the tomato genome version 2.40 and SL10539 786 LC7260 at position 35194800 of chromosome 6, on the tomato genome version 2.40 in chromosome 6 of a plant of the line TUT115 NCIMB accession number 42109, and
   d) the fragment corresponding to that comprised between and including SNPs EP 0489 LC7684 at position 3897960 of chromosome 9, on the tomato genome version 2.40 and EE 1452 at position 63642500 of chromosome 9, on the tomato genome version 2.40 in chromosome 9 of a plant of the line TUT115 NCIMB accession number 42109, and
   e) the fragment corresponding to that comprised between and including SNPs SL10204 1269 at position 124598 of chromosome 12, on the tomato genome version 2.40 and EE 0924 at position 1166000 of chromosome 12, on the tomato genome version 2.40 in chromosome 12 of a plant of the line TUT115 NCIMB accession number 42109, and
wherein the arthropod pest is South American pinworm *Tuta absoluta*.

2. The *S. lycopersicum* plant according to claim 1, wherein the introgressed sequences from *S. galapagense* are homozygously present in the genome of the plant.

3. The *S. lycopersicum* plant according to claim 1, characterized by the presence in the genome of said *S. lycopersicum* plant of at least one of the following alleles:
   a) allele G of SNP solcap_snp_sl_18619 at position 68232900 of chromosome 1, on the tomato genome version 2.40;
   b) allele C of SNP solcap_snp_sl_12348 at position 72528600 of chromosome 1, on the tomato genome version 2.40;
   c) allele C of SNP EP_1592_LC7762 at position 83766400 of chromosome 1, on the tomato genome version 2.40,
   d) allele T of SNP EE_0301 at position 3636270 of chromosome 5, on the tomato genome version 2.40,
   e) allele G of SNP EE_4363_LC7656 at, position 166755 of chromosome 6, on the tomato genome version 2.40,
   f) allele A of SNP CL016475-0340 at position 22094800 of chromosome 9, on the tomato genome version 2.40;
   g) allele C of SNP EP_0502 at position 41847000 of chromosome 9, on the tomato genome version 2.40,
   h) allele A of SNP EE_4969_LC7529 at position 49173600 of chromosome 9, on the tomato genome version 2.40,
   i) allele T of SNP EE_2332 at position 54692600 of chromosome 9, on the tomato genome version 2.40,
   j) allele C of SNP SL10204_1269 at position 124598 of chromosome 12, on the tomato genome version 2.40,
   k) allele A of SNP SGN-U573565_snp665 at position 155493 of chromosome 12, on the tomato genome version 2.40 or
   l) allele T of SNP EE_0924 at position 1166000 of chromosome 12, on the tomato genome version 2.40.

4. The plant according to claim 1, wherein said introgressed sequences constitute Quantitative Trait Loci (QTL) underlying the trait corresponding to resistance to arthropod pest.

5. The plant according to claim 1 comprising allele G of SNP solcap_snp_sl_18619 at position 68232900 of chromosome 1, on the tomato genome version 2.40, allele C of SNP solcap_snp_sl_12348 at position 72528600 of chromosome 1, on the tomato genome version 2.40, allele C of SNP EP_1592_LC7762 at position 83766400 of chromosome 1, on the tomato genome version 2.40, allele T of SNP EE_0301 at position 3636270 of chromosome 5, on the tomato genome version 2.40, allele G of SNP EE_4363_LC7656 at position 166755 of chromosome 6, on the tomato genome version 2.40, allele A of SNP CL016475-0340 at position 22094800 of chromosome 9, on the tomato genome version 2.40; allele C of SNP EP_0502 at position 41847000 of chromosome 9, on the tomato genome version 2.40, allele A of SNP EE_4969_LC7529 at position 49173600 of chromosome 9, on the tomato genome version 2.40, allele T of SNP EE_2332 at position 54692600 of chromosome 9, on the tomato genome version 2.40, allele C of SNP SL10204_1269 at position 124598 of chromosome 12, on the tomato genome version 2.40, allele A of SNP SGN-U573565_snp665 at position 155493 of chromosome 12, on the tomato genome version 2.40 and allele T of SNP EE_0924 at position 1166000 of chromosome 12, on the tomato genome version 2.40.

6. The plant according to claim 1, wherein said plant is obtained as a progeny of a plant of line TUT115 NCIMB accession number 42109.

7. The plant according to claim 1, wherein said plant is also resistant to another arthropod pest.

8. The plant according to claim 7, wherein said another arthropod pest is chosen from the group comprising whiteflies, thrips and spider mites.

9. The plant according to claim 1, wherein said resistance is measured by Percent Leaflet Attacked.

10. A cell of the *S. lycopersicum* plant according to claim 1, comprising in its genome introgressed sequences from *S. galapagense* conferring resistance to said arthropod pest, including the fragments a) to e) referred to in claim 1,
wherein the introgressed sequences are chosen from those present in the genome of a plant of the line TUT115 NCIMB accession number 42109.

11. A plant part of a *S. lycopersicum* plant selected from the group consisting of seeds, reproductive material, roots, flowers, fruits, rootstock or scion, said plant part comprising the cell according to claim 10.

12. Seed of a *S. lycopersicum* plant, which develops into the plant according to claim 1.

13. Hybrid plant of *S. lycopersicum*, obtained by crossing a plant of *S. lycopersicum* with the resistant plant according to claim 1, comprising in its genome said introgressed sequences from *S. galapagense* conferring resistance to said arthropod pest.

* * * * *